United States Patent
Davison et al.

(10) Patent No.: US 6,755,074 B2
(45) Date of Patent: Jun. 29, 2004

(54) LIQUID CHROMATOGRAPHIC METHOD AND SYSTEM

(75) Inventors: Dale A. Davison, Greenwood, NE (US); Scott L. Blakley, Omaha, NE (US)

(73) Assignee: Isco, Inc., Lincoln, NE (US)

( * ) Notice: Subject to any disclaimer, the term of this patent is extended or adjusted under 35 U.S.C. 154(b) by 0 days.

(21) Appl. No.: 09/883,968

(22) Filed: Jun. 19, 2001

(65) Prior Publication Data

US 2002/0116989 A1 Aug. 29, 2002

Related U.S. Application Data

(63) Continuation-in-part of application No. 09/794,772, filed on Feb. 27, 2001.

(51) Int. Cl.[7] .......................... G01N 13/00; G01N 30/84
(52) U.S. Cl. .................... 73/61.55; 73/61.56; 73/61.57; 73/61.58; 204/451; 204/452; 204/453; 204/601; 204/603; 356/318; 356/328; 356/334; 356/436; 356/439
(58) Field of Search ............................. 73/61.55, 61.56, 73/61.57, 61.58; 204/451, 452, 453, 601, 603; 356/318, 328, 334, 436, 439

(56) References Cited

U.S. PATENT DOCUMENTS

| | | | |
|---|---|---|---|
| 3,985,021 A | | 10/1976 | Achener et al. |
| 4,045,343 A | | 8/1977 | Achener et al. |
| 4,523,097 A | * | 6/1985 | Allington ................. 250/458.1 |
| 4,726,097 A | * | 2/1988 | Zimmermann et al. ... 19/159 R |
| 4,771,629 A | * | 9/1988 | Carlson et al. ............ 73/23.35 |
| 4,882,063 A | | 11/1989 | Allington et al. |
| 4,882,781 A | | 11/1989 | Allington |
| 4,883,409 A | | 11/1989 | Strohmeier et al. |
| 4,908,187 A | * | 3/1990 | Holmquist et al. ........... 422/81 |
| 4,981,597 A | | 1/1991 | Allington et al. |
| 5,040,126 A | | 8/1991 | Allington |
| 5,071,562 A | | 12/1991 | Allington et al. |
| 5,080,785 A | | 1/1992 | Allington et al. |
| 5,107,908 A | | 4/1992 | Newhouse et al. |
| 5,158,675 A | | 10/1992 | Allington et al. |
| 5,221,448 A | * | 6/1993 | Weinberger et al. ........ 204/452 |
| 5,234,587 A | | 8/1993 | Allington et al. |
| 5,360,320 A | | 11/1994 | Allington et al. |
| 5,600,444 A | * | 2/1997 | Tong .......................... 356/432 |
| 5,637,208 A | | 6/1997 | Dourdeville |

(List continued on next page.)

FOREIGN PATENT DOCUMENTS

JP          63071650        4/1988

Primary Examiner—Hezron Williams
Assistant Examiner—André K. Jackson
(74) Attorney, Agent, or Firm—Vincent L. Carney

(57) ABSTRACT

To economically perform preparatory chromatography, a plurality of pumps each having a corresponding one of a plurality of pistons and a corresponding one of a plurality of cylinders are driven by one motor to draw and pump solvent simultaneously into corresponding columns. To form a gradient, the pumps are connected to two-way valves that are connected alternately to a first solvent and a second solvent, whereby the time said valve is in a first position controls the amount of solvent drawn from the first reservoir into said pumps and the amount of time in said second position controls the amount of said second solvent drawn from the second reservoir into said pumps and the solvent is mixed in the pumping systems. The detectors are photodiodes mounted to light guides in the flow cells that generate signals related to light absorbance and communicate with a controller, whereby the controller receives signals indicating solute between the light guides and causes collection of solute. An over-pressure system compensates for pressure over a predetermined level.

31 Claims, 20 Drawing Sheets

U.S. PATENT DOCUMENTS

| | | | | |
|---|---|---|---|---|
| 5,685,965 A | * | 11/1997 | Allington | 204/451 |
| 5,717,209 A | * | 2/1998 | Bigman et al. | 250/339.12 |
| 5,828,452 A | * | 10/1998 | Gillispie et al. | 356/328 |
| 5,897,781 A | | 4/1999 | Dourdeville | |
| 5,935,522 A | | 8/1999 | Swerdlow et al. | |
| 6,019,897 A | | 2/2000 | Horsman et al. | |
| 6,056,790 A | * | 5/2000 | Clark et al. | 8/502 |
| 6,118,536 A | | 9/2000 | Sakamoto et al. | |
| 6,175,409 B1 | | 1/2001 | Nielsen et al. | |
| 6,188,813 B1 | * | 2/2001 | Dourdeville et al. | 385/12 |
| 6,296,771 B1 | | 10/2001 | Miroslav | |
| 6,318,157 B1 | | 11/2001 | Corso et al. | |
| 2002/0092770 A1 | * | 7/2002 | Hedberg et al. | 204/603 |

* cited by examiner

LIQUID CHROMATOGRAPHIC METHOD AND SYSTEM

RELATED CASES

This application is a continuation-in-part of U.S. patent application Ser. No. 09/794,772 filed Feb. 27, 2001, entitled LIQUID CHROMATOGRAPHIC METHOD AND SYSTEM by Dale A. Davison and Scott L. Blakley and assigned to the same assignee as this application.

BACKGROUND OF THE INVENTION

This invention relates to liquid chromatographic methods and apparatuses.

Inexpensive liquid chromatographic apparatuses have been developed and are in use, particularly for preparatory chromatography where the emphasis is on quickly obtaining relatively large samples at low cost. Such systems generally include at least one solvent reservoir, a pump, a controller, a chromatographic column, a collector and usually a detector. Commonly, provision is made for a gradient to be developed and such gradient systems require at least two solvent reservoirs and some mechanism for mixing the solvent from each of the two reservoirs together to form a gradient for application to the column.

The prior art apparatuses have a disadvantage in that they are not as inexpensive as desired or require a longer period of time than desired for the separation.

SUMMARY OF THE INVENTION

Accordingly, it is an object of the invention to provide a novel chromatographic system and method.

It is a still further object of the invention to provide a low-cost method of providing substantial amounts of solvent to a chromatographic system.

It is a still further object of the invention to provide an inexpensive gradient chromatographic system.

It is a still further object of the invention to provide a low-cost detection system equipped to handle relatively large amounts of solvent and separated materials.

It is a still further object of the invention to provide an economical system for driving multiple inexpensive pumps while avoiding damage from excessively high pressures such as may be caused by blockage of liquid jamming of any one of the multiple pumps.

In accordance with the above and further objects of the invention, a chromatographic system includes a plurality of pumps, all driven together by a single pump motor for drawing solvent from solvent reservoirs, pumping the solvent through a plurality of columns for separation of sample, pumping the solvent and solute through a plurality of detectors for detecting solute and pumping the solute into a fraction collector for collection. The solvent is pulled from the reservoir through a plurality of outlets of a manifold so that a plurality of flow streams may be pulled into the corresponding plurality of pumps from one or more solvent reservoirs. The pumps may each receive the combined output of a plurality of different solvent reservoirs in controlled ratios, and in the preferred embodiment, with multiple charges of each solvent for each pump cycle to form a gradient and the different solvents in the case of such a gradient are mixed in the path between a flow inlet conduit to the pump and the pump outlet with the pump cylinder and inlet tube being dimensioned to provide adequate mixing during refill of the pump. The ratios of solvents are controlled by a solenoid operated valve in the preferred embodiment. Mixing in the pump cylinders is aided by a rapid refill stroke pulling solvent into an off-center inlet port of the piston pumps, causing turbulence.

With this arrangement, a single motor is able to drive a multiplicity of pumps which together can supply a large amount of solvent to a number of columns simultaneously. In the preferred embodiment, at least two different reservoirs pull solvents and different gradients are applied to at least some columns. However, embodiments in which the same solvent is applied to each column is possible and a gradient may be applied to some columns and a single solvent to others. In one embodiment, the gradient is formed without separate mixers and the mixing is done in the pump and the inlet to the pump and/or other equipment associated with the system. In the event of over-pressure in the liquid, which may be indicative of blockage or jamming in the system, the system senses the over-pressure and compensates by: (1) reducing the flow rate until the pressure is reduced; or (2) by stopping the pump or pumps and providing an indication of over-pressure so the problem can be corrected such as by attaching a tube to drain the cylinder of the pump; or (3) by manually disconnecting or removing the malfunctioning portion of the system; or (4) by continuing the motion of the motor and automatically by-passing any column causing that over-pressure for that pump, such as for example with a fluid pressure release valve.

An inexpensive detecting arrangement is utilized that comprises a light source which focuses light from a central spot on a lamp for stability and selects the frequency of light with a diffraction grating, reflecting the selected light through a slot and onto a plurality of light conductors. The selected light is transmitted through the light conductors to flow cells. Each flow cell has within it two light guides that are aligned and have a space between them for some of the fluid from the chromatographic column to flow. One of the light guides in each of the flow cells receives light from a corresponding one of the light conductors and transmits it to the other light guide through the effluent from the column without intervening focusing means to provide light-guide to light-guide communication in the flow cell through the fluid passing in between the two light guides. The light that is not absorbed in the flow cell is detected by photodiodes located directly against the receiving light guides.

From the above description, it can be understood that, the chromatographic system and chromatographic method of this invention is low cost and yet provides substantial yield in a short time.

SUMMARY OF THE DRAWINGS

The above noted and other features of the invention will be better understood from the following detailed description when considered with reference to the accompanying drawings in which:

FIG. 17 is fragmentary simplified enlarged view of a portion of the embodiment of FIG. 16;

DETAILED DESCRIPTION

Figure 1:
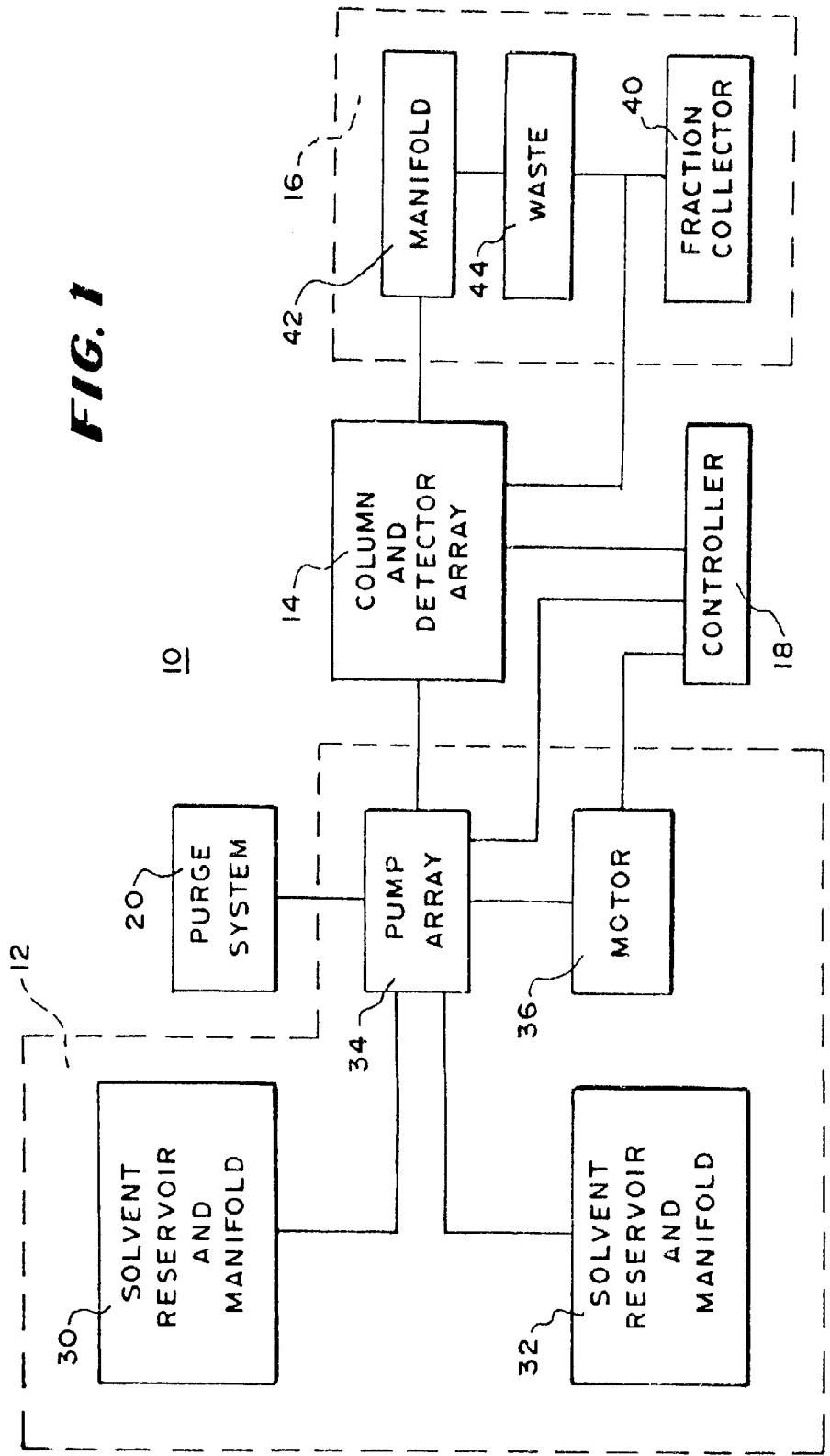
FIG. 1 is a block diagram of a liquid chromatographic system in accordance with an embodiment of the invention.

In FIG. 1, there is shown a block diagram of a preparatory liquid chromatographic system 10 having a pumping system 12, a column and detector array 14, a collector system 16, a controller 18 and a purge system 20. The pumping system 12 supplies solvent to the column and detector array 14 under the control of the controller 18. The purge system 20 communicates with a pump array 34 to purge the pumps and the lines between the pumps and the columns between chromatographic runs. The pump array 34 supplies solvent to the column and detector array 14 from which effluent flows into the collector system 16 under the control of the controller 18. The controller 18 receives signals from detectors in the column and detector array 14 indicating bands of solute and activates the fraction collector system 16 accordingly in a manner known in the art. One suitable fraction collection system is the FOXY® 200 fraction collector available from Isco, Inc., 4700 Superior Street, Lincoln, Nebr. 68504.

To supply solvent to the pump array 34, the pumping system 12 includes a plurality of solvent reservoirs and manifolds, a first and second of which are indicated at 30 and 32 respectively, a pump array 34 and a motor 36 which is driven under the control of the controller 18 to operate the array of pumps 34 in a manner to be described hereinafter. The controller 18 also controls the valves in the pump array 34 to control the flow of solvent and the formation of gradients as the motor actuates the pistons of the reciprocating pumps in the pump array 34 simultaneously to pump solvent from a plurality of pumps in the array and to draw solvent from the solvent reservoirs and manifolds such as 30 and 32.

During this pumping process, the pressure may increase above the amount desired because of blockage or jamming. If the pressure increases above a predetermined amount in one or more of the pumps in the pump array 34, there is an automatic correction mechanism for reducing or releasing pressure from at least that one or more pumps to avoid damage. In the preferred embodiment, the pressure is reduced by reducing the flow rate. If this does not reduce the pressure to an acceptable value, a warning is provided so the operator may correct the problem such as by using tubing to by-pass the column. For this purpose, the pressure is sensed with a pressure transducer, and when it exceeds a preset value above the rated pressure such as at 55 psi, the pressure release or reduction mechanism starts so the motor 36 may continuously move the pistons up and down without damage. Moreover, valves in the pump array 34 control the amount of liquid, if any, and the proportions of liquids from different reservoirs in the case of gradient operation that are drawn into the pump and pumped from it. The manifolds communicate with the reservoirs so that a plurality of each of the solvents such as the first and second solvents in the solvent reservoir manifold 30 and 32 respectively can be drawn into the array of pumps 34 to permit simultaneous operation of a number of pumps.

While in the preferred embodiment, an array of reciprocating piston pumps are used, any type of pump is suitable whether reciprocating or not and whether piston or not. A large number of different pumps and pumping principles are known in the art and to persons of ordinary skill in the art and any such known pump or pumping principle may be adaptable to the invention disclosed herein with routine engineering in most cases provided that one motor drives a plurality of pumps. While two solvents are disclosed in the embodiment of FIG. 1, only one solvent may be used or more than two solvents. Because of the operation of a plurality of pumps simultaneously driven by a single motor, efficiency and cost reduction are obtained by this pumping mechanism.

To process the effluent, the collector system 16 includes a fraction collector 40 to collect solute, a manifold 42 and a waste depository 44 to handle waste from the manifold 42. One or more fraction collectors communicate with a column and detector array 14 to receive the solute from the columns, either with a manifold or not. A manifold may be used to combine solute from more than one column and deposit them together in a single receptacle or each column may deposit solute in its own receptacle or some of the columns each may deposit solute in its own corresponding receptacle and others may combine solute in the same receptacles. The manifold 42 communicates with the column and detector array 14 to channel effluent from each column and deposit it in the waste depository 44. The fraction collector 40 may be any suitable fraction collector such as that disclosed in U.S. Pat. No. 3,418,084 or the above-identified FOXY fraction collector.

The column and detector array 14 includes a plurality of particularly economical flow cells, a different one of the flow cells communicating with each of the columns. The flow cells include within them light guides positioned so that the effluent flows between them and around them, the light guides being sufficiently close to obtain suitable sensitivity at high light absorbance for a preparatory operation as will be described hereinafter and the total cross-sectional area of the flow path and the total volume of flow being sufficient to permit bubbles, if any, to flow around the light guides so as to avoid distorting the detection of light.

Figure 2:
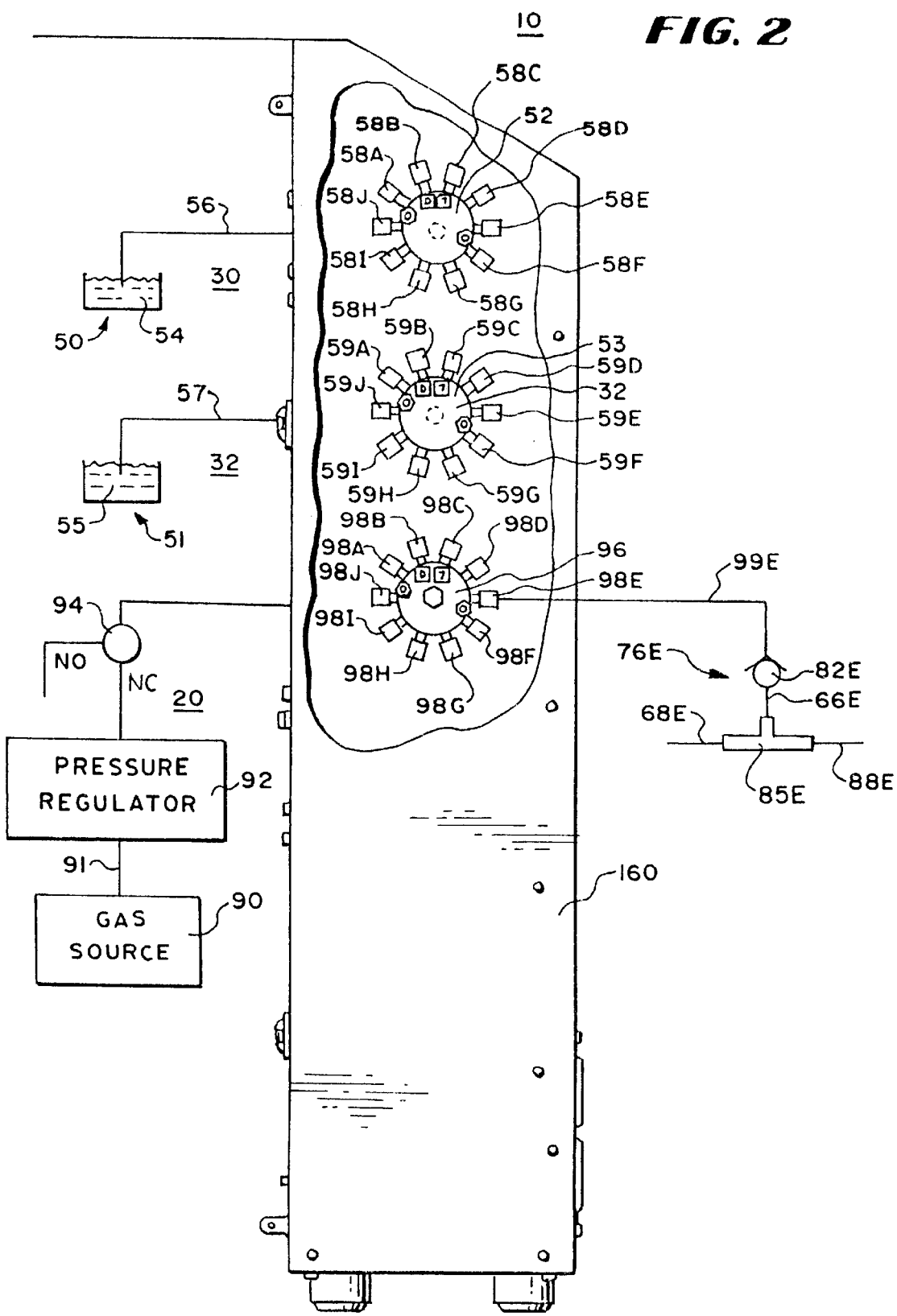
FIG. 2 is a simplified partly-schematic, partly-side elevational view of solvent reservoirs, manifolds and a purge system used in the embodiment of FIG. 1.

In FIG. 2, there is shown a partly schematic and partly elevational view of the first solvent reservoir and manifold 30, the second solvent reservoir and manifold 32 and the purge system 20 illustrating the manner in which the manifolds are mounted in a housing 160. The first solvent reservoir and manifold 30 includes a first manifold 52 having one inlet and ten outlets 58A–58J, a conduit 56 and a first solvent reservoir 50, which solvent reservoir 50 holds a first solvent 54. The conduit 56 communicates with the solvent 54 in the solvent reservoir 50 on one end and communicates with the interior of the manifold 52 at its other end. Each of the outlets 58A–58J of the manifold 52 communicate with the interior of a different one of ten cylinders of the pumps (not shown in FIG. 2) through appropriate valves. Similarly, the second manifold 53 communicates with the second solvent 55 in the second solvent reservoir 51 through a conduit 57. The manifold 53 has a plurality of outlet conduits 59A–59J which communicate with the interiors of a corresponding number of the pump cylinders through appropriate valves as described in more detail hereinafter so that the solvent from the reservoir 50 and the solvent from the reservoir 51 may be mixed together in a proportion that is set in accordance with the timing of the valves.

The purge manifold 96 communicates with a gas source 90 through a conduit 91 and a pressure regulator 92 and the three-way valve 94 to maintain an appropriate pressure for purging the lines. This manifold 96 has ten outlets 98A–98J each communicating with a different one of the ten conduits connecting a corresponding one of the corresponding pumps to a corresponding one of ten corresponding columns to transmit gas back through the piston pumps to purge the cylinders of the piston pumps and the conduits connecting the pumps to the columns. Each of the conduits connected to the purge connector arrangement lead to a corresponding pump in the pump array 34 (FIG. 1) which in turn communicates with the corresponding one of the columns in the column and detector array 14 (FIG. 1). One such purge connector arrangement 76E is shown in FIG. 2 connected by a conduit 99E to the outlet 98E from the manifold 96 to purge the conduits 68E and 88E.

Between chromatographic runs, the pressurized gas source 90, which is commonly a source of nitrogen gas, communicates through the pressure regulator 92 and the three-way valve 94 with the manifold 96 to provide purging fluid to each of the corresponding outlets 98A–98J for each of the pump and column combinations indicated by the T joints, one of which is shown at 85E.

With this arrangement, respective ones of the purge conduits 99A–99J (only 99E being shown in FIG. 2 connecting manifold outlet 98E to check valve 82E) are connected to apply air or nitrogen gas or other purging substance to the respective ones of the T-joints 80A–80J (80E being shown in FIG. 2) to purge conduits 68A–68E (68E being shown in FIG. 2) and 88A–88E (88E being shown in FIG. 2) and their corresponding pumps through a corresponding one of the purge connectors 76A–76J (76E being shown in FIG. 2). Each of the purge connections, such as 76E, corresponds with a corresponding one of the manifold purge outlets 98A–98J, the corresponding one of the check valves 82A–82J and corresponding ones of the conduits 88A–88E. The check valves 82A–82J are arranged to prevent effluent from the pumps from flowing back to the manifold 96 and the electrically operated three way valve 94 permits selecting the time for purging under the control of the controller 18 (FIG. 1). The purge system 20 permits purging of the pumps as well as the lines between the pumps and the column and detector array 14 and in the column and detector array 14.

While in the preferred embodiment, the manifolds 52, 53 and 96 each have ten outlet conduits which communicate with ten pump cylinders through appropriate valves as will be described hereinafter, each could have more or less than ten outlets. Each of the reservoirs is similar to the reservoir 30 and operates in a similar manner to provide the same solvent from the same reservoir to a plurality of pump cylinders for simultaneous pumping of the solvent into a plurality of columns.

Figure 3:
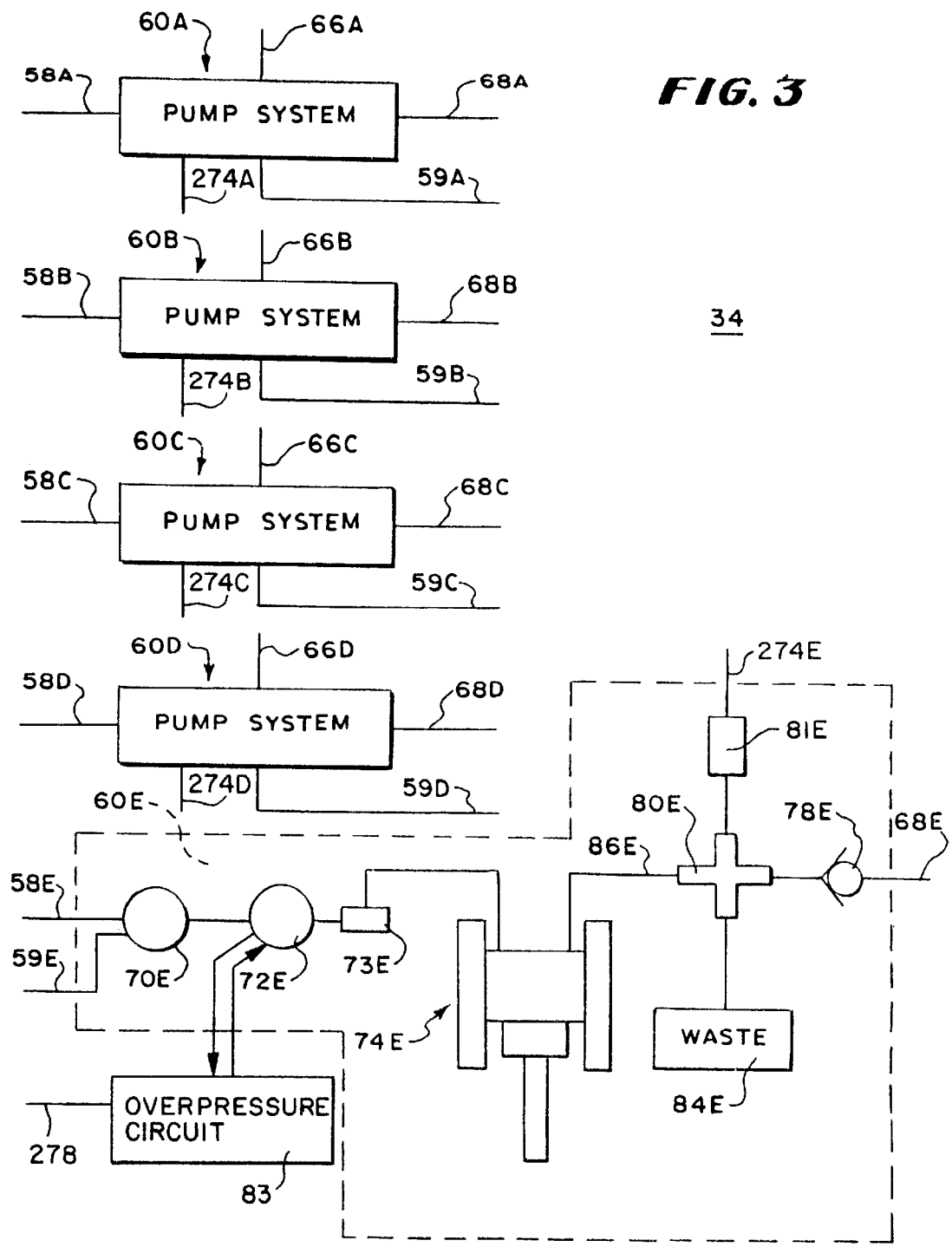
FIG. 3 is a block diagram of a pump array useful in the embodiment of FIG. 1.

In FIG. 3, there is shown a schematic block diagram of a pump array 34 having a plurality of piston pump systems 60A–60J and an over-pressure circuit 83, the piston pump systems 60A–60E, being shown for illustration in FIG. 3 although in the preferred embodiment there are ten such pumps each arranged to communicate with corresponding ones of the ten outlets from the manifold 52 (FIG. 2) and with corresponding ones of the outlets from the manifold 53 (FIG. 2) to pump solvent from the reservoirs 50 and 51 (FIG. 2) into corresponding ones of the columns (not shown in FIG. 3). In FIG. 3, four of the pump systems 60A–60D are shown in block form and a fifth 60E is shown in greater detail with the understanding that each of the ten pump systems are substantially identical so that the explanation of the pump system 60E is an adequate explanation for all of the pump systems.

Each of the pump systems communicates with a corresponding one of the manifold outlets 58A–58J and 59A–59J to receive two different solvents for the purpose of forming a gradient. They may also communicate with a source of purge fluid as indicated by the purge conduits 66A–66J. With this arrangement, each of the pumps draws solvent into it from the solvent reservoirs 50 and 51 (FIG. 2). The solvent flows from the pumps through a corresponding one of the outlets 68A–68J.

The pump system 60E includes the inlet conduit 58E from the first solvent reservoir 50 and manifold 52 (FIGS. 1 and 2), the inlet conduit 59E from the second solvent reservoir 51 and manifold 53 (FIG. 2), a three-way solenoid valve 70E, a two-way solvent valve 72E, a long flow conduit 73E, a reciprocating piston pump 74E, and a check valve 78E. With this arrangement, the two different solvents from conduit 58E and 59E are applied to the pump 74E through a common point connecting the three-way solenoid valve 70E and the two-way solvent valve 72E. In the preferred embodiment, two cycles of solvent are applied for each stroke of the piston pump. The size of the cylinder, the size of the flow conduit 73E, the speed of the refill and delivery strokes of the piston are selected to ensure mixing within the pump 74E and flow conduit 73E so as to pump a formed gradient through the conduit 86E, through the check valve 78E and the outlet conduit 68E to the column and detector array 14 (FIG. 1). For this purpose the pump cylinders are in the range of one inch to eight inches long. In the preferred embodiment, the cylinders are 3.5 inches long.

To provide two infections or charges of solvent during a refill portion of a pump cycle, the two-way electronically-controlled solvent valve 72E opens once during each piston refill stroke of the pump 74E and closes during the delivery portion of the pump cycle. In the preferred embodiment the two-way solvent valve 72E is a solenoid valve. To provide a gradient, the three-way electronically-controlled time-proportioning switching valve 70E twice during each refill stroke opens first to the first solvent reservoir 50 (FIG. 2) and then to the second solvent reservoir 51 (FIG. 2) to provide both solvents in two stages for better mixing. The proportion of the time the switching valve 70E is open to the first solvent reservoir 50 (FIG. 2) and then to the second solvent reservoir 51 (FIG. 2) determines the composition of the mixture in the gradient. Both of the solenoid operated valves 70E and 72E are under the control of the controller 18 to which they are electrically connected. A pressure transducer 81E communicates with the pump outlet through the joint 80E and is electrically connected to the over-pressure circuit 83 through electrical connection 274E as better described in connection with FIG. 13 hereinafter.

Figure 13:
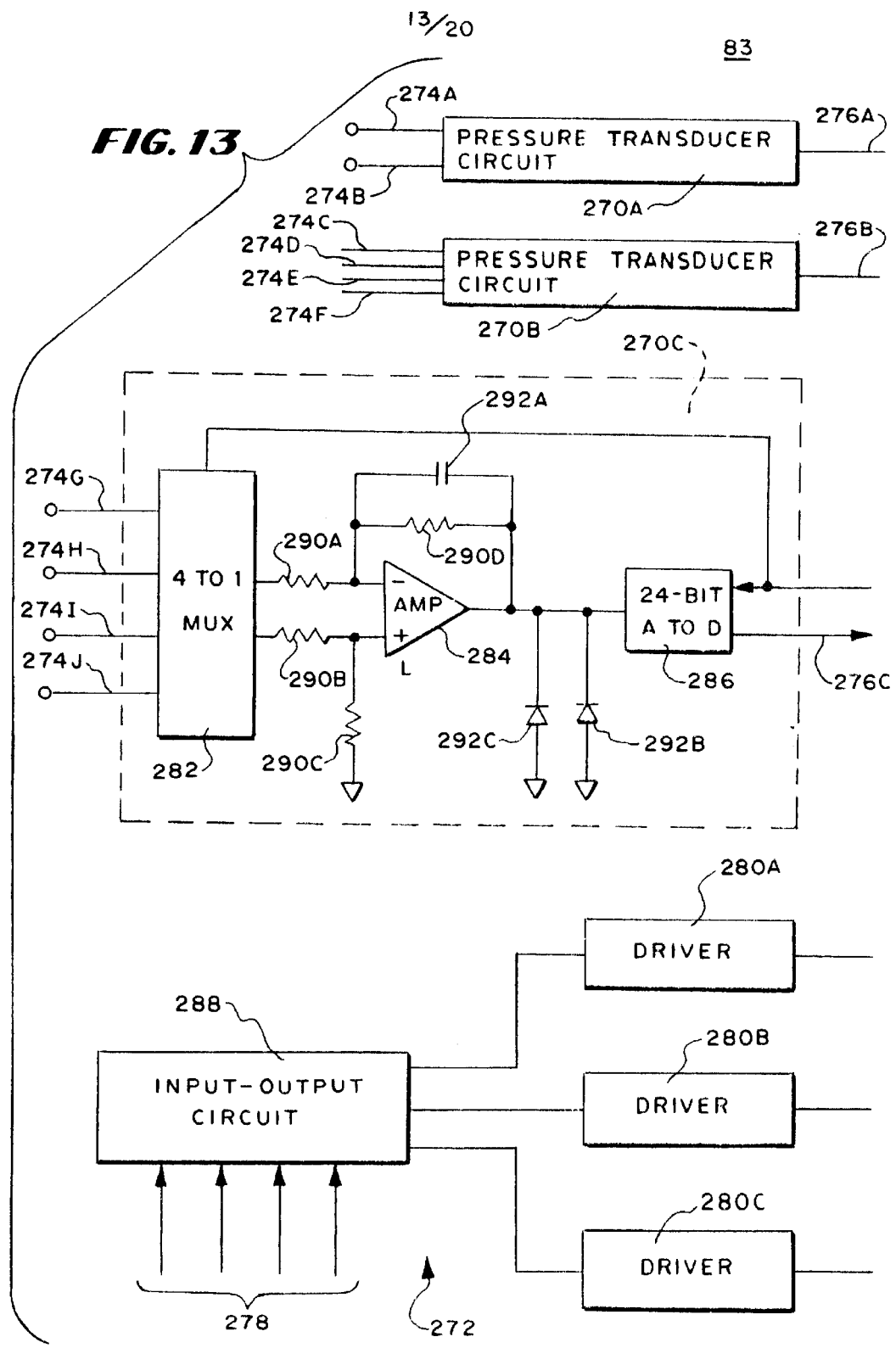
FIG. 13 is partly block, partly-schematic diagram of an over-pressure system used in an embodiment of the invention.

The over-pressure circuit 83 is electrically connected to the solenoid valve 72 to controller 18 (FIG. 20) and to the transducer 81E to control the time the solenoid valve 72E is open and thus to control the flow rate or motor speed. It receives signals for this purpose from the controller 18 through conductors 278 (FIG. 13). The transducer 81E in the preferred embodiment is a miniature 0–300 psi (pounds per square inch) transducer available from Dresser Instruments, Ashcroft Headquarters, 250 East Main Street, Stratford Conn. 0661-5145; Telephone (203) 783-6659 as an Ashcroft K8 transducer, although there are other suitable transducers available.

Figure 4:
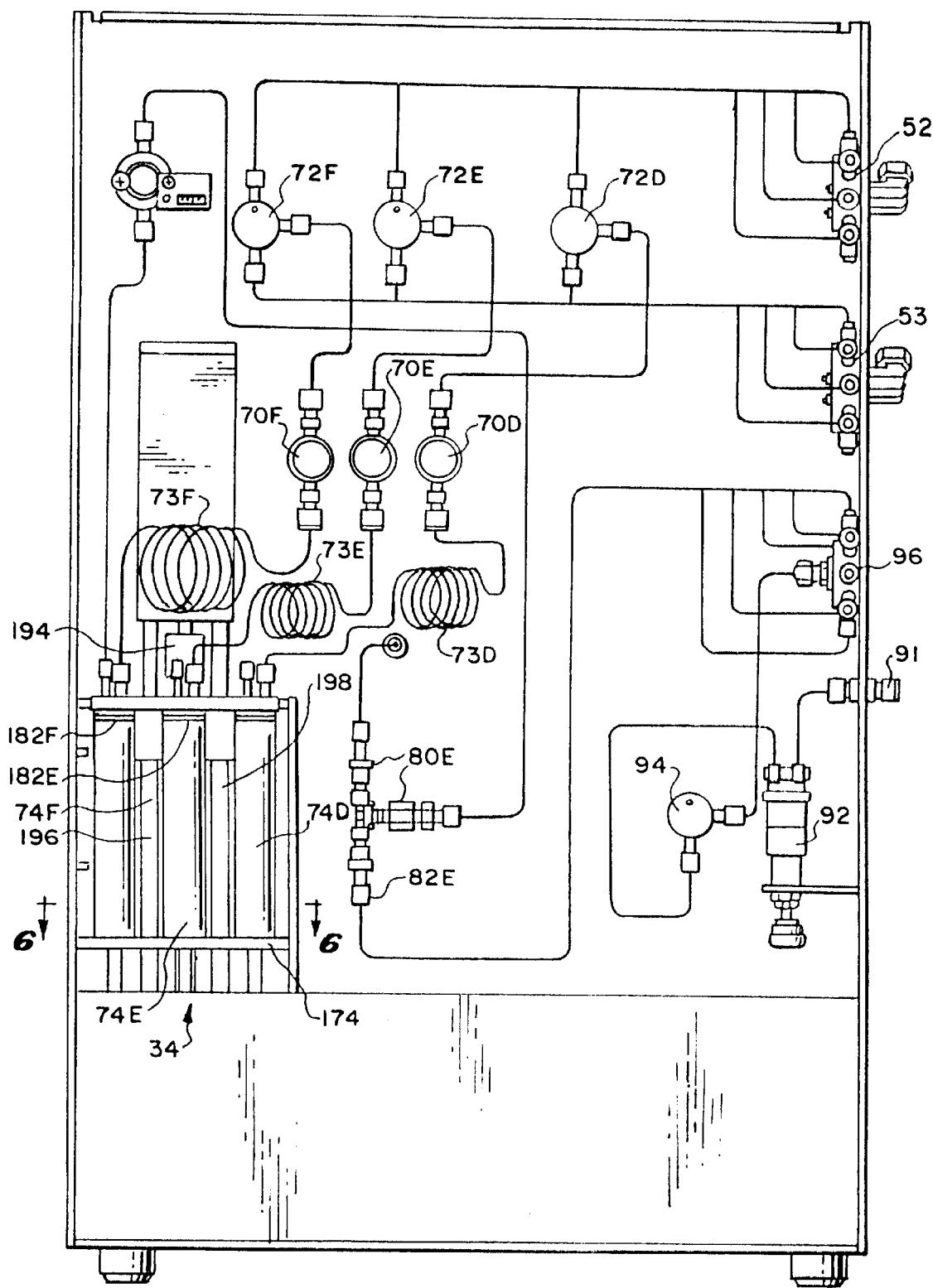
FIG. 4 is a simplified partly-schematic, partly-rear elevational view of solvent reservoir manifold and purge system connections used in the embodiment of FIG. 1.

In FIG. 4, there is shown an elevational view of the backside of the chromatographic system 10, simplified for purposes of explanation including the pump array 34 with a plurality of pumps 74A–74J (74F, 74E and 740 being shown in FIG. 4) with pistons 182E and 182F being driven by the carriage 174 (referred to herein from time to time as frame or drive plate) as will be explained more completely hereinafter. For convenience, three inlets to the pumps 74F, 74E and 74D are shown, with 74E being at the opposite side of the carriage 174 from 74F and 74E and 74D. The pumps 74F, 74E, and 74D are connected at their inlet ports to respective ones of the flow conduits 73F, 73E and 73D respectively to receive fluid from corresponding ones of the valves 70F, 70E, and 70D. The valves 70F, 70E and 70D are, in turn, connected to the switching valves 72F, 72E and 72D to receive solvent from respective ones of the valves 72F, 72E and 72D connected to respective ones of the outlets of the manifold 52 and from respective ones of the outlets of the manifold 53 so that the valves 72F, 72E and 72D combine the first and second solvents and permit them to flow to corresponding ones of the shutoff valves 70F, 70E and 70D (FIG. 7. Similarly, the manifold 96 has its outlets connected to corresponding ones of the check valves 82A–82J (82E being shown in FIG. 4) and of corresponding ones of the T-joints 80A–80J (T-joint 80E being shown in FIG. 4) within the conduits 86E and 68E (FIG. 3) and its inlet connected to a source of air or nitrogen 91 through the pressure regulator 92 and valve 94 to provide a purging flow of air or nitrogen between chromatographic runs.

Figure 5:
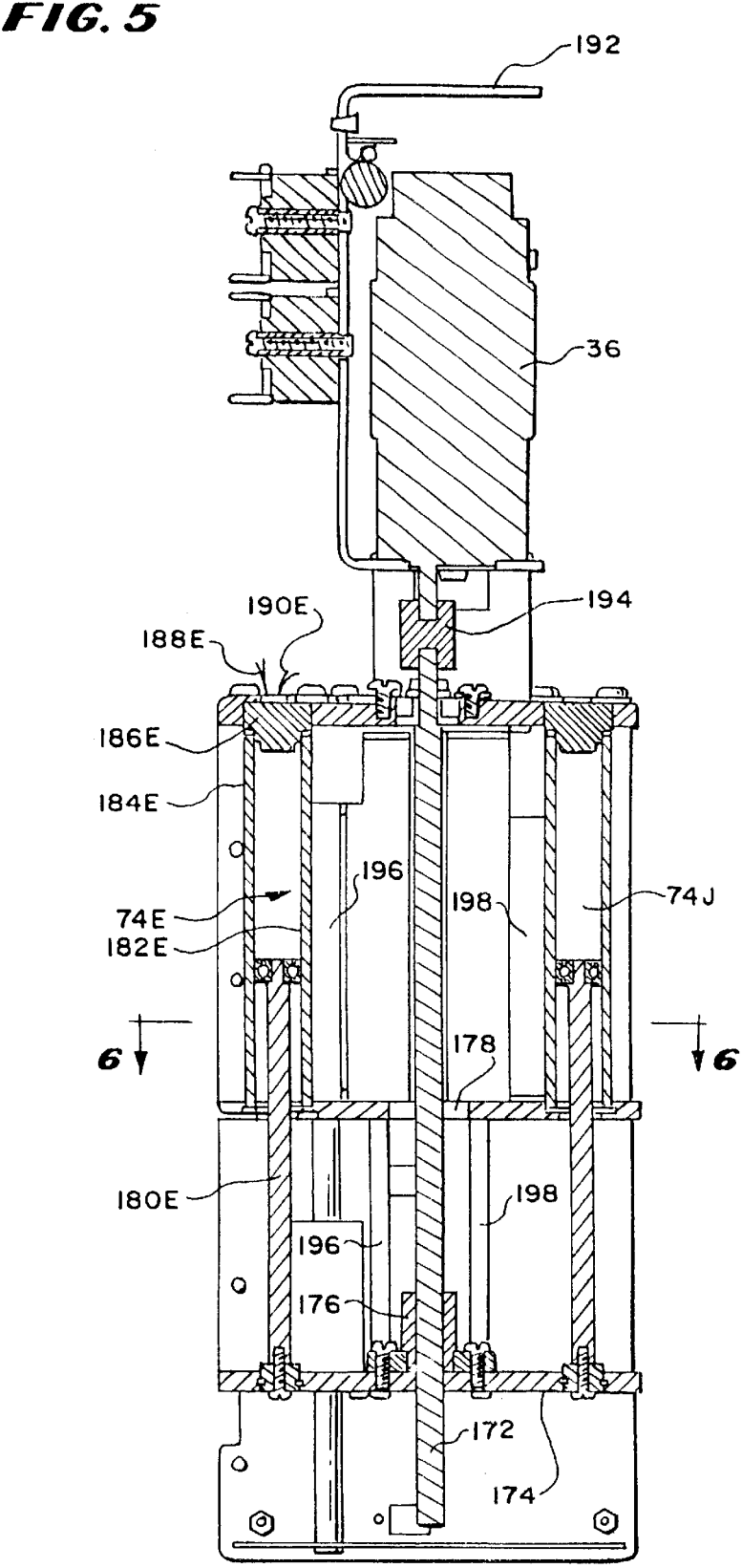
FIG. 5 is an elevational sectional view of a pump array and motor for driving the pistons for the pumps in the pump array useful in the embodiment of FIG. 1.
Figure 6:
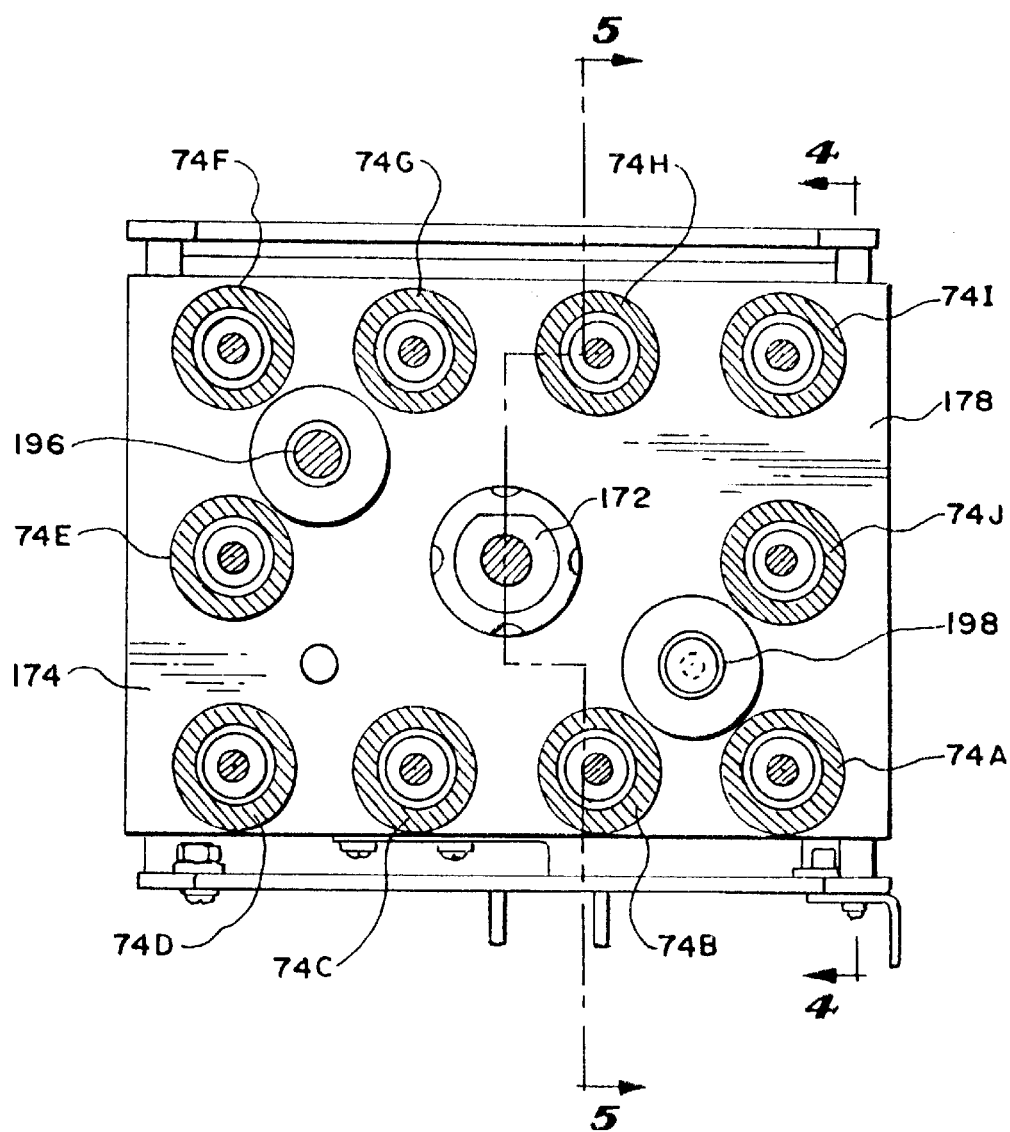
FIG. 6 is a sectional view through lines 6—6 of FIG. 5.

In FIG. 5, there is shown an elevational sectional view taken Through lines 5—5 of FIG. 6 of the pump array 34 including pumps 74A–74J and the single motor 36 which is a Pittman Model GM 14901E161 available from Pittman Division of Penn Engineering, having an address at 343 Godshall Drive, Harleysville, Pa. 19438-0003. The pump array includes a ball screw 172, a piston rod drive plate 174, a ball nut assembly 176, and a cylinder retaining plate 178. With this arrangement the motor 36 drives the ball screw 172 to pull the piston rod drive plate (also referred to as frame or carriage) 174 upwardly and pushes it downwardly as the ball screw assembly 172 is rotated by the motor 36. The ball nut assembly 176 is rigidly attached to the piston rod drive plate 174. As the piston moves, the pump cylinders are held in place by the cylinder retaining plate 178 so That each of the pumps pump simultaneously.

In this view, only pump 74E and the pump 74J are shown, and only the pump 74E will be described in detail with the understanding that each of the pumps 74A–74J are substantially the same. The pump 74E includes the piston rod 180E, the piston 182E, the cylinder 184E, a piston plug 186E, an inlet 188E and an outlet 190E. With this arrangement, the piston rod 180E drives the piston 182E within the cylinder 184E. As the piston 182E is moved downwardly, solvent is pulled through the inlet 188E in the piston plug 186E at the top of the cylinder 184E and when the piston 182E is moved upwardly, fluid is forced from the pump outlet 190E within the plug 186E.

In the preferred embodiment, the pumps 74A–74J have a cylinder displacement programmable for 5 to 18 ml and pump at pumping rates between 5 to 50 ml/min. The valves 70A–70J twice each refill cycle select: (1) an open position to first solvent 54 (FIG. 2) or a closed position in which no solvent flows for 100 percent solvent 54; or (2) an open position for the first solvent followed by an open position for the second solvent 55 for a mixture. These values may vary and are selected so that a gradient can be formed suitable for preparatory chromatography to obtain the desired substance. With this arrangement, the time the valves are open determines the respective amounts of the first and second solvents that are injected in that time period so that both the first solvent 54 and second solvent 55 are injected into the pump cylinder 184E in selected amounts twice in each intake stroke of the pump in which the piston plug 186E moves downwardly.

In the refill of a pump cycle portion, because of the length of the flow paths in the cylinders and in the flow conduits 73D–73F, the cylinder length and the speed of the refill stroke, the solvents are mixed to form substantially continuous steps of stepped gradient (the gradient may proceed in steps but each step from a pump cycle is substantially continuous) as the solvent is pulled inwardly. For this purpose, the refill stroke of the piston is at least 3 times faster than the delivery stroke to cause turbulent flow in the cylinder during refill. The two-way valves 72D–72F permit fluid to flow into the cylinder 184E during a refill stroke and close the cylinder 184E during a delivery stroke so that the cylinder 184E receives a fixed amount of fluid which it pumps outwardly. The stroke is controlled by the motor 36 and ball screw 172 under the control of the controller 18 (FIG. 1). This is acceptable with preparatory chromatography because the demands on the continuousness of the flow are not as great as in analytical chromatography.

The motor 36 is mounted to the housing of the chromatographic system by the mounting bracket 192 and coupled to the ball screw 172 through the coupling 194 to rotate the screw rod within the ball screw 172 and thus pull the drive plate 174 upwardly and downwardly. The drive plate 174 is guided in its path by two guide rods 196 and 198 (FIG. 4).

In FIG. 6, there is shown a sectional view through lines 6—6 of FIGS. 4 and 5 showing the placement of the cylinders for the pumps 74A–74J as held within the cylinder retaining plate 178. As shown in this view, the ball screw 172 passes through the plate so as to pull upwardly the piston drive plate 174 in a delivery stroke and move downwardly the piston drive plate 174 in a pump cylinder filling stroke. The guide rods 196 and 198 guide the drive plate upwardly and downwardly.

In FIGS. 7–12 there is shown a developed view of the two way valve 72E, the inlet tubing 73E, and the pump 74E showing six different positions of the pump which result in mixing of solvents A and B in the preferred embodiment to provide a gradient that is suitable for preparatory chromatography. The diameter of the inlet tubing 73E is selected so as to facilitate mixing of solvents A and B which are inserted one after the other into the tubing 73E by proportioning valve 70E to provide charges into the pump chamber. The pump chamber is also sufficiently long to facilitate mixing. In the preferred embodiment, the tubing 73E has a length of 35 inches and should have a length of between 10 inches and 250 inches and a narrow inner diameter, such as for example 0.085 inches. The cylinder 160E is relatively long and narrow, being 3.6 inches long with a diameter of 0.612 inches in the preferred embodiment. It should have a length in the range of 3 to 8 inches and a ratio of length to diameter of between 3 and 8 inches.

Figure 7:
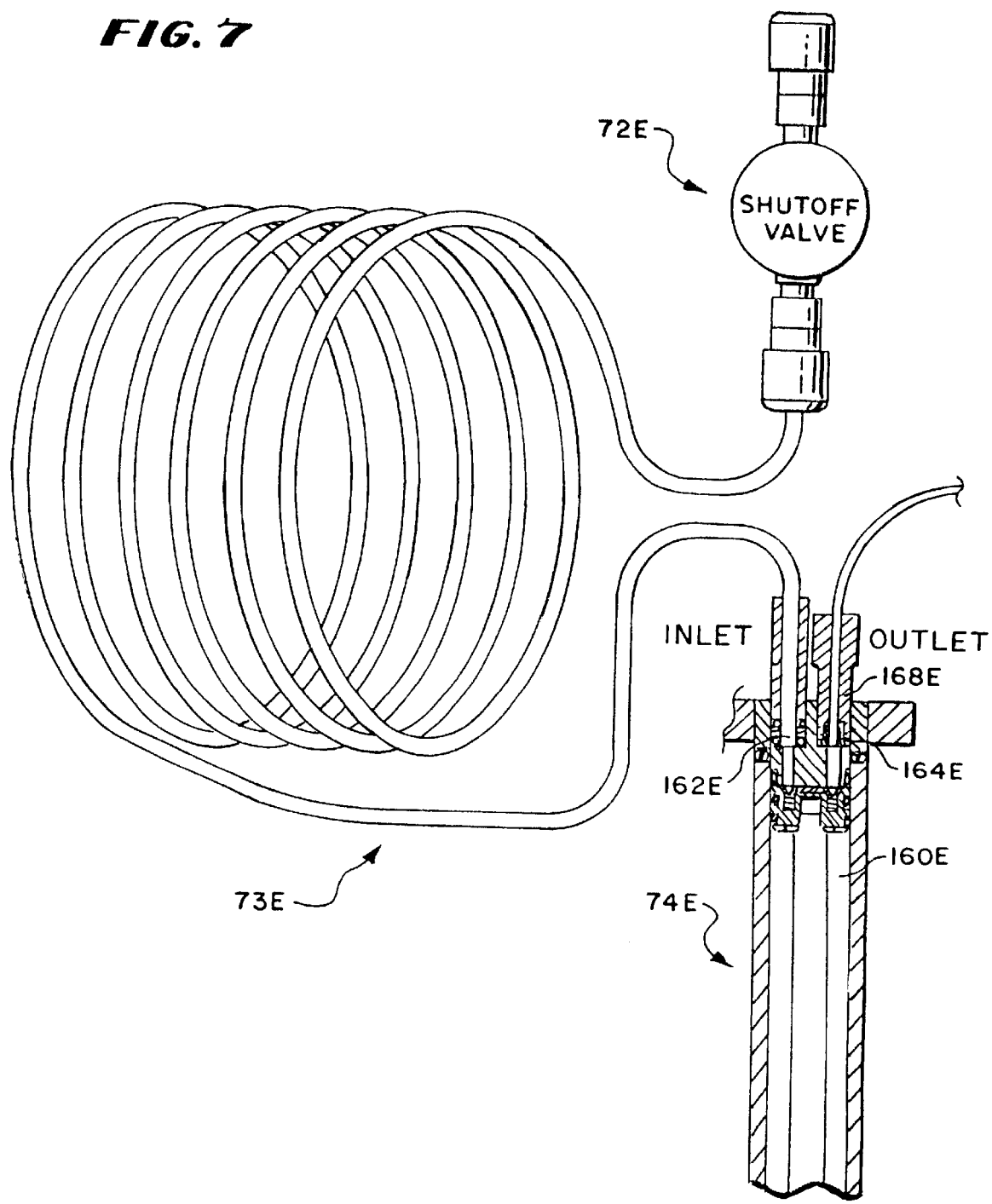
FIGS. 7–12 are progressive schematic drawings of an on-off valve, delayed coil and pump in six different positions of operation: (a) FIG. 7 being a first position at the start of a refill stroke of the pump; (b) FIG. 8 being a second position in the refill stroke of the pump; (c) FIG. 9 being a third position in the refill stroke of the pump; (d) FIG. 10 being a forth position in the refill stroke of the pump; (e) FIG. 11 being a fifth position in the refill stroke of the pump; and (f) FIG. 12 being a sixth position in the refill stroke of the pump.
Figure 8:
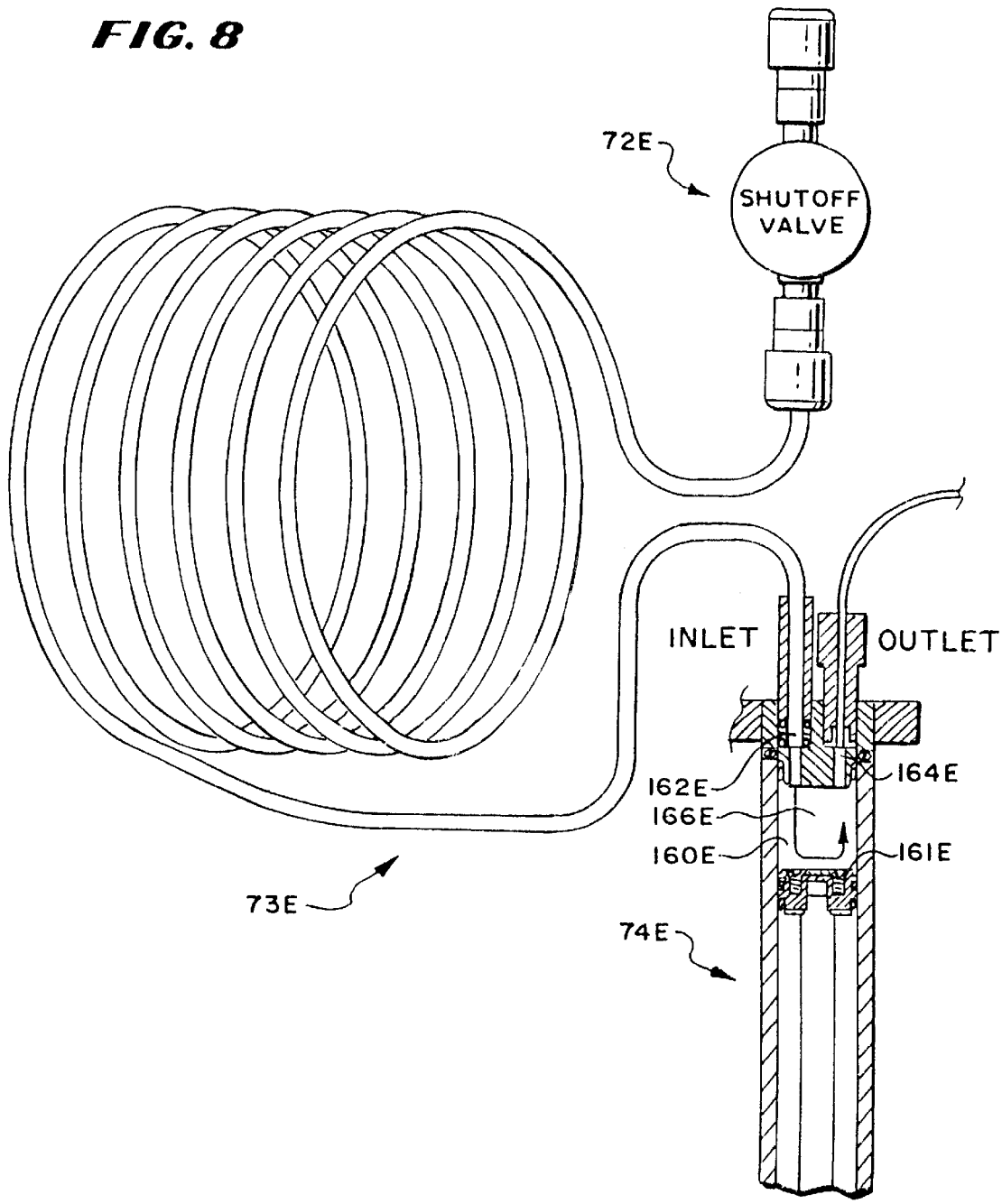
Figure 9:
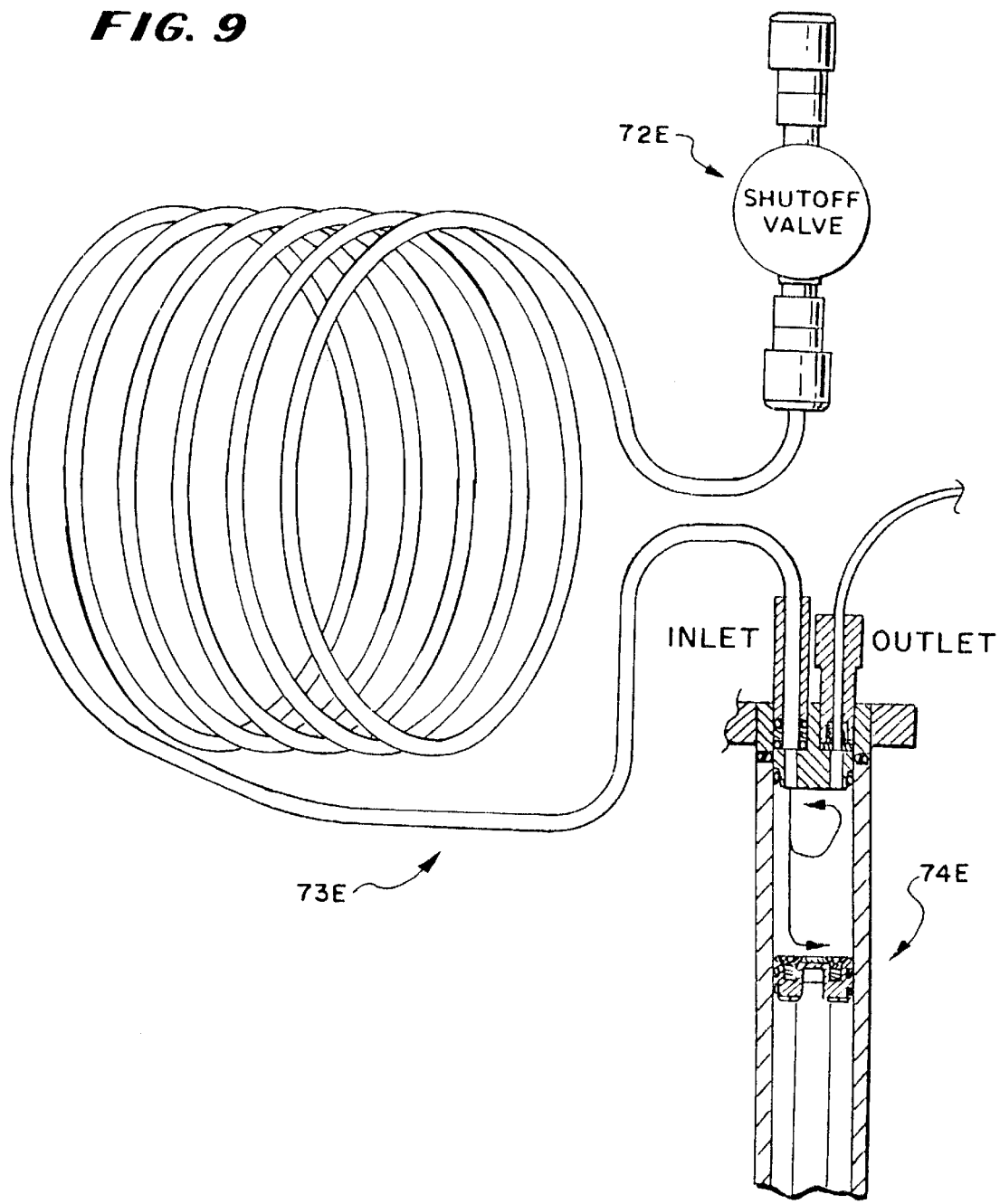
Figure 10:
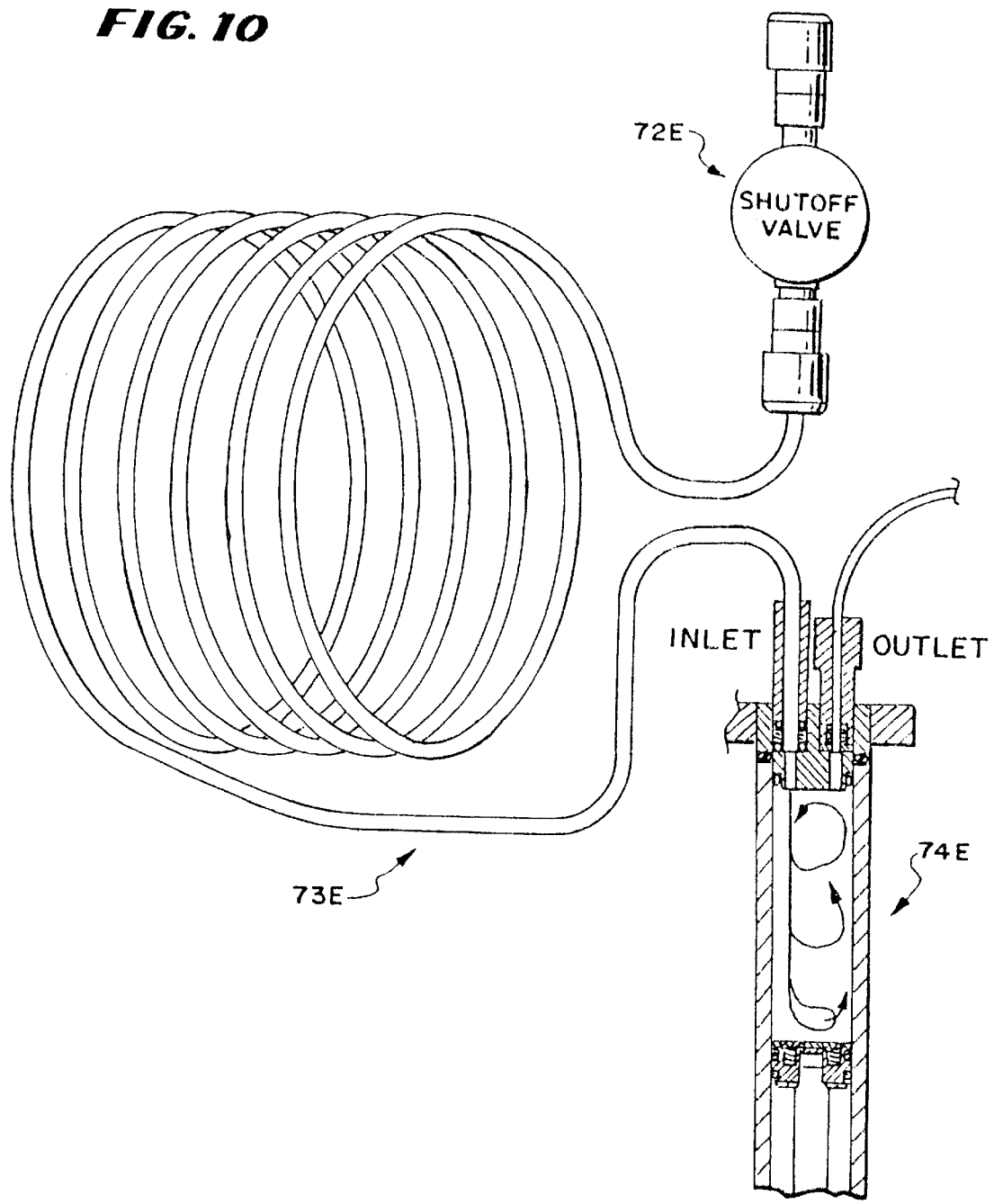
Figure 11:
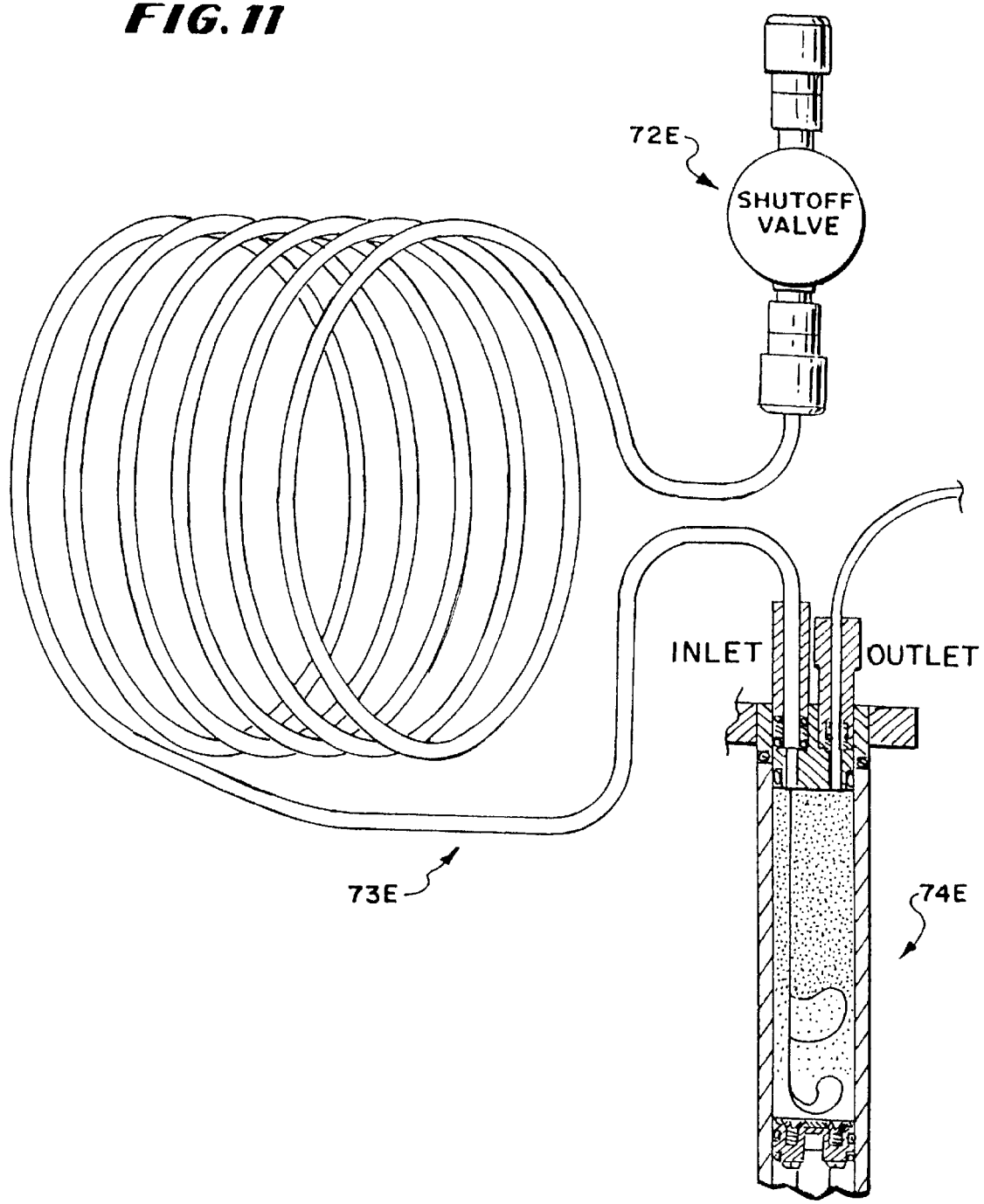
Figure 12:
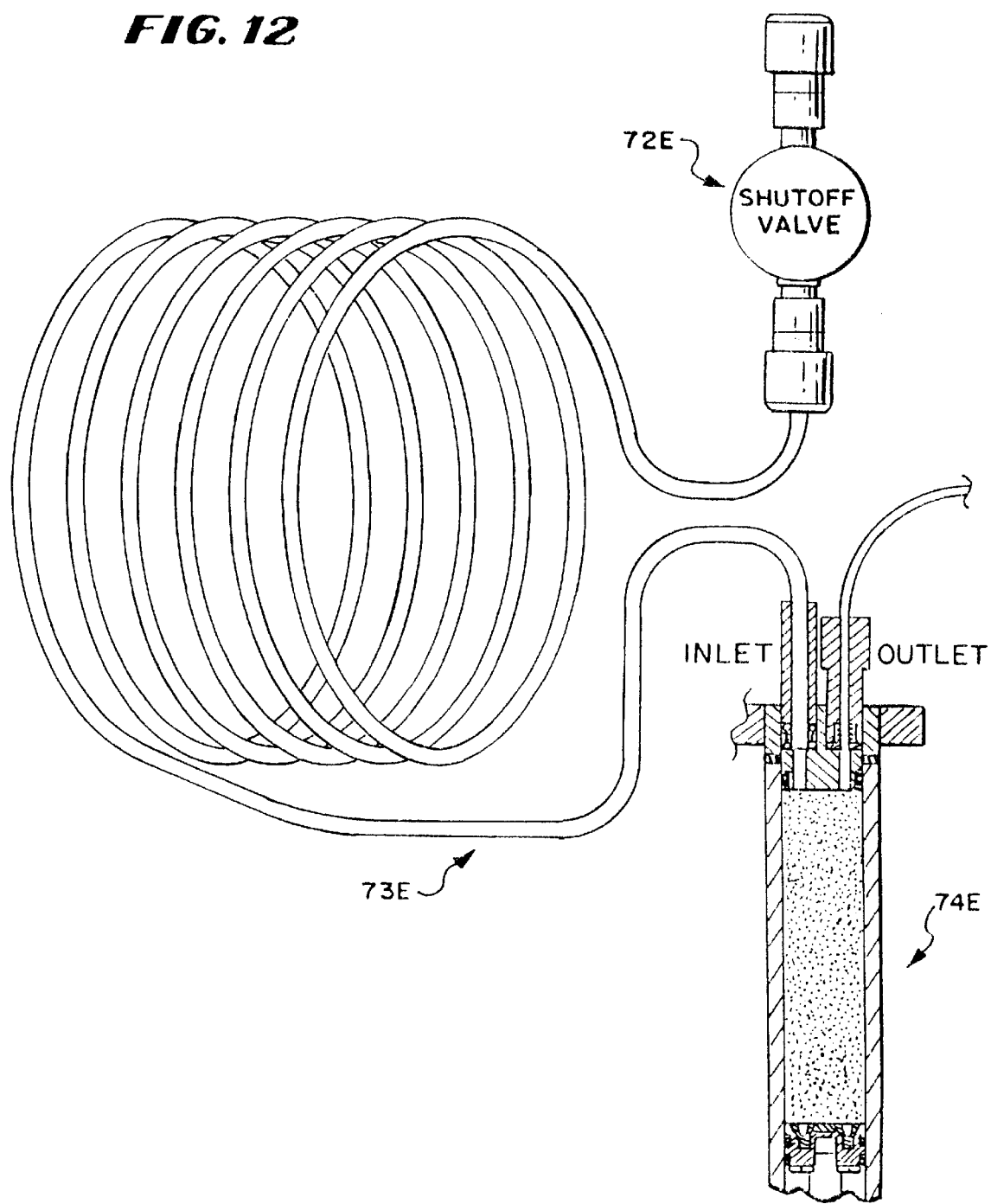

The cylinder 160E is shown in FIG. 7, the initial position, against the head 168E in which blocks flow into the inlet 162E into the tubing 73E and outflow from the outlet 164E. A short time later, the piston 161E has been withdrawn causing fluid to flow through the inlet 162E which is on one side of the cylinder 160E to cause mixing as a circular current is formed such as in the eddy current as shown in FIG. 8 at 166E. Still later, as shown in FIG. 9, further eddy currents occur in the pump chamber as the piston continues to withdraw and as shown in FIG. 10 still further eddy currents near the piston. The eddy currents result in mixing before the pump stroke of the piston. In FIG. 12, the upward stroke is beginning in position six and the downward stroke has ended so as to move a relatively well mixed fluid out through the outlet.

In FIG. 13, there is shown a partly-block, partly-schematic drawing of the over-pressure circuit 83 having three pressure transducer circuits 270A–270C and a pressure control circuit 272. Only the pressure transducer circuit 270C is shown in detail in FIG. 13, with the understanding that all three pressure control circuits 270A–270C are substantially the same. The pressure control circuit 272 includes an input-output circuit 288 and ten drivers, three of which are shown at 280A–280C, one for each of the pressure transducers 81A–81J (see FIG. 3 for 81E).

To control the flow rate and thus compensate for over-pressure conditions, the input-output circuit 288 receives a binary code on lines 278 from the controller 18 (FIGS. 1 and 20) and in response applies signals to the selected ones of the drivers 280A–280J to control the on-off time of the solenoids 72A–72G (FIG. 4) and thus to control the flow rate from each of the pumps 74A–74J (FIG. 4) through respective ones of the conduits 86A–86J (86E being shown in FIG. 3).

To supply a signal to the controller 18 indicating pressure, the pressure transducer circuits 270A–270J (only 270A–270C being shown in FIG. 13 with 270C being shown as a schematic diagram) includes the four-to-one multiplexer 282, the amplifier 284 and the 24 bit analog to digital converter 286 that applies signals through conduits 276C to the controller 18 to supply a signal representing four of the transducers. The signals to the controller 18 representing the other six transducers are supplied by the pressure transducer circuits 270A and 270B as shown in FIG. 13. The four-to-one multiplexer 282 receives inputs on conductors 274G–274J from respective ones of the transducers 81G–81J (81E shown in FIG. 3) and applies these signals one at a time to the operational amplifier 284.

The operational amplifier 284 is connected with a parallel connected 1500 pf (picofarads) capacitor and a 732 K (kilo-ohm) resistor between its output and inverting terminal. The multiplexer 282 is connected to the inverting and non-inverting terminals of the amplifier 284 through 10 K resistors 290A and 290B respectively. The non-inverting terminal of the operational amplifier 284 is connected to ground through the 232 K resistor 290C.

The output of the operational amplifier 284 is electrically connected to the input of the 24 bit analog to digital converter 286 as well as to ground through reverse resistance of the diode 292C and the 0.2 uf (microfarad) capacitor 292B for spike protection. The output of the 24 bit analog to digital converter 286 is connected through the conductor 276C to the controller 18. With this structure, data is clocked into the circuit twice per second from the analog to digital converter 286 by clock pulses from the control electronics and is corrected by offset and gain by a conventional EEPROM (not shown in FIG. 13).

In operation, the pressure limits of the system are set in the controller 18. If a pump channel exceeds that limit, then: (1) the pump flow and data acquisition rate goes to half speed of the original rate by controlling the motor speed (FIG. 3) through the over-pressure circuit 83 from the controller 18; (2) if the pressure returns to its set rate, the pump continues the stroke at half rate until the pump is empty; (3) the pump then refills all the pump channels that are being run; (4) pumping is resumed at the original programmed flow and data acquisition rate; (5) if an over-pressure is detected before the cylinders are empty, the pump rate is set to one-quarter its set maximum rate; (6) if the pressure does not return to normal, the motor is stopped and an alarm given until the problem is cured and the operator indicates a start; and (7) on later pump strokes, the process is repeated from step 1.

This procedure allows the separation to be completed on all channels selected. If the over-pressure is due to the transient effect, such as sample crashing in on the column, later pump strokes have a stronger solvent and this may clear up the blockage. If the problem is caused by a flow rate that is too high for the solvents in the columns used, the run progresses at a lower than the programmed flow rate to accommodate the solvent in the column.

If the pump is operating at one-quarter speed and an over-pressure condition occurs, this indicates a fairly severe plug. Under this condition, the controller 18 places the pump under a hold condition and the operator is signaled. The operator then manually intervenes and corrects the problem before continuing. The problem may be corrected by replacing columns causing the problem with tubing so the separation on the remaining channels can continue and by other repair work.

Figure 14:
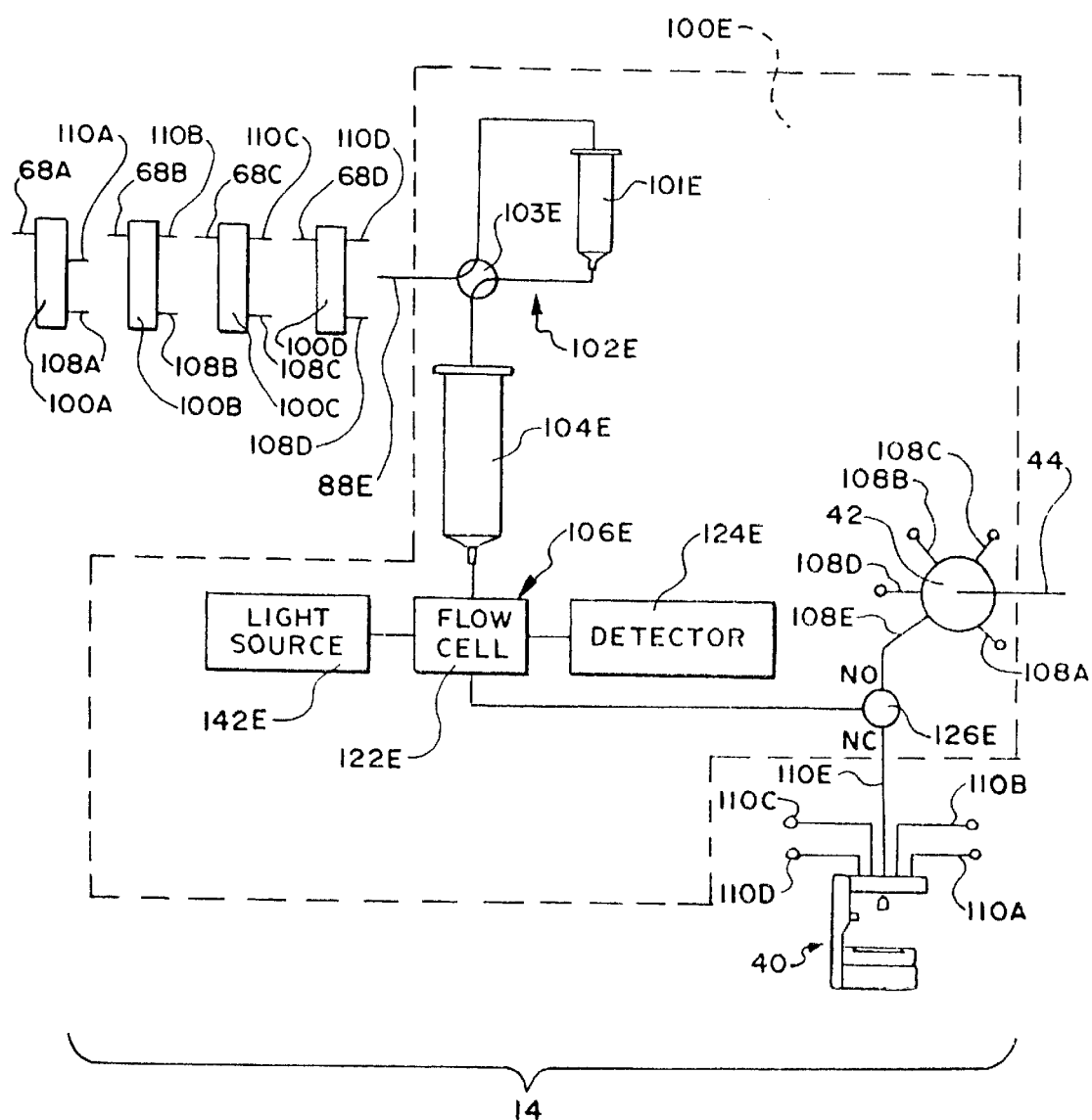
FIG. 14 is a block diagram of a column and detector array in accordance with the embodiment of FIG. 1.

In FIG. 14, there is shown a schematic diagram of a column and detector array 14 having a plurality of columns and detectors, five of which are indicated as 100A–100E, a corresponding plurality of outlet conduits 68A–68E; a corresponding plurality of solute outlets 110A–110E; a corresponding plurality of waste outlets 108A–108E from the manifold 42 (FIG. 1) and a fraction collector 40. In the preferred embodiment, there are ten columns and detectors. For illustration, the column and detectors 100A–100D are shown as a general block whereas the column and detector 100E is shown in greater detail with the understanding that the collector and detectors 100A–100D are substantially the same. Moreover, while five collectors and detectors are shown to correspond with the example being used in this application, more or fewer could readily be used and ten are used in the preferred embodiment.

The collector and detector 100E includes the injector system 102E, a column 104E, a detection system 106E, the waste outlet 108E and the solute outlet 110E. With this arrangement, solvent, whether a gradient or not, flows in the conduit 88E through the injector 102E, a column 104E, the flow cell 122E, where solute may be detected and from there into the collection system 40 for the collection of solute and the disposal of waste. The column 104E may be any type of chromatographic column regardless of the mode of operation and it is generally picked in accordance with the separation problem. In the preferred embodiment the column is the REDISEP disposable column sold by Isco, Inc., 4700 Superior Street, Lincoln, Nebr. 68504. It is mounted to either receive a sample injection manually from a syringe or automatically from the injector 102E as well as receiving solvent on the outlet 88E. Its outlet flows through the detection system 106E.

The detection system 106E includes a light source 142E, a flow cell 122E, a detector 124E and a valve 126E for channeling fluid either to the waste outlet 44 through conduit 108E or to the collector on outlet 110E. The light source 142E hereinafter referred to as the optical bench applies light from a source common to each of the column and detector assemblies 100A–100E and applies it through each of the corresponding ones of the flow cells including the flow cell 122E and from there to the corresponding detectors including the detector 124E. The signal received indicates the effluent to be channeled to the collector and that to be channeled to waste for the particular column and detector system.

The injector system 102E includes a solid sample load cartridge 101E and a four-way manual selective valve 103E for controlling the selection of sample and injection into the column 104E. In the embodiment of FIG. 14, an individual injector system (injector system 102E being shown in FIG. 14) is provided for each of the columns although the outlet from one injector could go to a manifold to supply the same sample to a plurality of columns and/or the outlet from one injection cartridge could go to a plurality of injection valves if desired. Similarly, a single fraction collector 40 is shown but a plurality of such collectors could be used with the individual valves connected to more than one collector. The injector 102E includes the four-way valve 103E for alternately injecting sample from the sample cartridge 101E and selecting the solvent gradient from the outlet 88E from the pumping system. Thus a sample may be injected and then with a turning of the manual valve 103E the chromatographic run may be initiated. While a manual four-way valve 103E is shown, automatic injector valves are also available and may be utilized.

Figure 15:
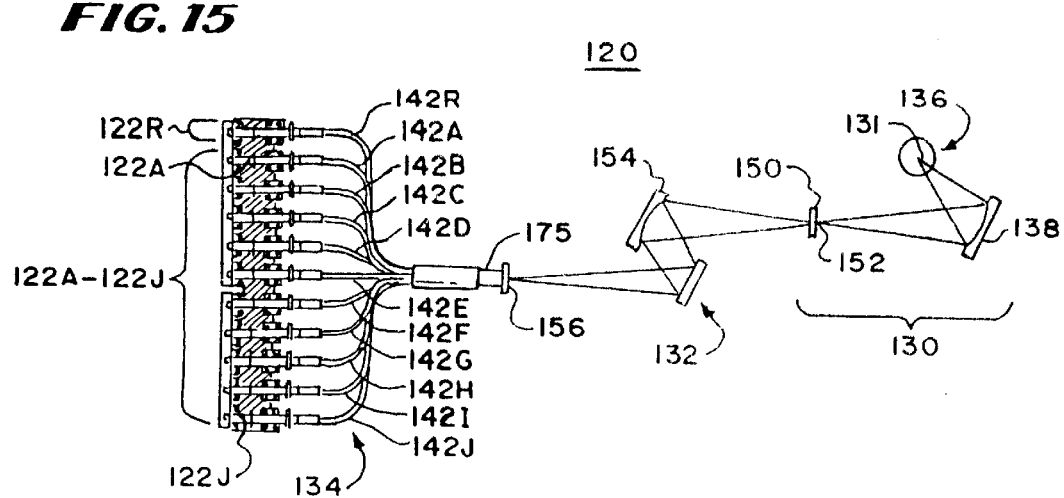
FIG. 15 is a schematic diagram of an array of light sources, flow cells and sensors in accordance with an embodiment of the invention.

In FIG. 15, there is shown a diagrammatic view of an optical bench 120 common to all of the flow cells 122A–122J and one reference flow cell 122R, having a single stable illuminated spot 131, a diffraction grating system 132 and a multiple pickup system 134 for providing stable light to each of the flow cells 122A–122J and the reference cells 122R. The illuminated spot 131 is the bright spot of a deuterium lamp 130. With this arrangement, a single small stable spot of light is transmitted onto the diffraction grating system 132 which in turn supplies the light to the multiple pickup system 134 for transmission through multiple paths for the multiple light sources such as 142A–142J and 142R for use by the corresponding detectors 124A–124J and 124R and flow cells 122A–122J and 122R in the system. The single light source 130 includes a suitable lamp 136, an aspherical condensing mirror 138, a source aperture plate 150 and an aspherical focusing mirror 154.

The lamp 136, which in the preferred embodiment is a deuterium lamp, transmits light from its central spot 131 to the condensing mirror 138 which reflects the light through a small aperture 152 in the aperture plate 150 to provide a narrow spot of light to the focusing mirror 154 for reflection onto a diffraction grating in the diffraction grating system 132. A suitable system of this type is described in greater detail in U.S. Pat. No. 5,239,359 except that instead of including aperture stops to restrict the light to a small flow cell opening, the light is focused onto a slit 157 in an aperture plate 156 for multiple light guides 142A–142J and 142R to multiple flow cells 122A–122J and 122R. The grating 132 reflects a stable line of light from the central spot of a selected frequency through a slit 157 in an aperture plate 156 mounted to the collar or tubular member 175 within the multiple pickup 134.

The aspherical condensing mirror 138 is used to focus an image of the 1-mm diameter light source in the deuterium lamp 130 on the UV entrance slit at the monochromator light entrance. The aspherical focusing mirror 154 produces a focused anastigmatic slit image, at the wavelength selected by the diffraction grating 132, on the slit-shaped entrance aperture of an 11-channel fiber optic bundle. Each channel consist of one, single discrete UV-grade quartz optical fiber of 400 $\mu$m diameter. The fiber optic bundle allows a single sample, low cost monochromator to be used for multiple UV absorbance chromatographic detectors. This results in cost savings in a parallel system.

The diffraction grating 132 is a plain grating with 1200 grooves per millimeter, and disperses the light from the lamp 136. The angle between the diffraction grating 132 and the central light beam coming from the aspherical focusing mirror 154 determines the center wavelength of the light entering the multiple individual optic fibers in the fiber optics bundle. The software controls an encoded motor, which actuates the grating in the monochromator. This allows the computer to control the detection wavelength used by the system. This encoded motor precisely sets the angle between the aspherical focusing mirror 154 and diffraction grating 132 by moving an arm to which the diffraction grating 132 is attached. The diffraction grating 132 swings on an arm to keep the monochromator focused throughout the wavelength range.

The light travels through the respective optic fibers in the fiber optic bundle. Each optic fiber is coupled to a flow cell, which is the light exit of the monochromator. A total of eleven individual optical fibers are organized in a nested linear array in the light inlet and fiber optic bundle to maximize the amount of light to each individual optical fiber and minimize the difference in light level and wavelength between them. Ten of the optical fibers are coupled to flow cells, which pass light through the chromatographic flow stream and then to measuring detectors. The reference fibers (eleventh fiber) is near the center of the linear array to minimize flicker noise from the deuterium lamp 130.

The multiple pickup 134 includes the aperture plate 156, the optical fibers 142A–142J and 142R positioned along the slit 157 so that the narrow slot of light is applied to them. The optical fibers transmit the light to corresponding ones of the flow cells 122A–122J and 122R with each of the flow cells including a corresponding light guide described hereinafter that transmits the light to a matching light guide in the flow cell. The matching light guide receives the light after it has passed through the effluent and transmits it to photodetectors.

Figure 16:
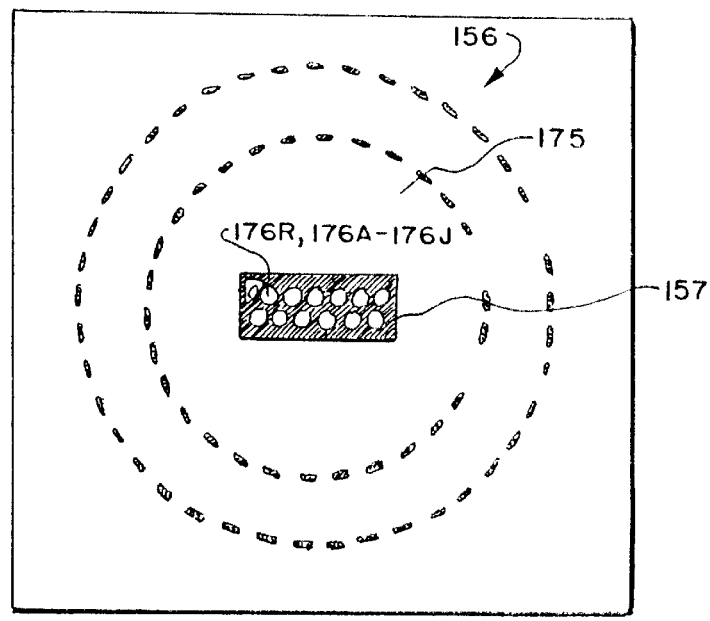
FIG. 16 is a fractional enlarged view of a portion of FIG. 15 showing light inlets to flow cells in accordance with an embodiment of the invention.

In FIG. 16 there is shown a plan view of the aperture plate 156 having a central elongated opening or slit 157 within a tubular member 175. The central elongated opening 157 has within it aperture stops 176R, 176A–176J each receiving a corresponding one of the light guides 142R, 142A–142J for a reference light source and light sources 142A–142J. This provides substantially equal intensity light sources to each of the flow cells 122R, 122A–122J to provide a reference 122R and ten measuring flow cells. In this manner, a stable source of light is reflected onto multiple light guides 142R, 142A–142J for use by the multiple detectors and flow cells of the system. The multiple light guides are a fiber optics bundle.

Figure 17:
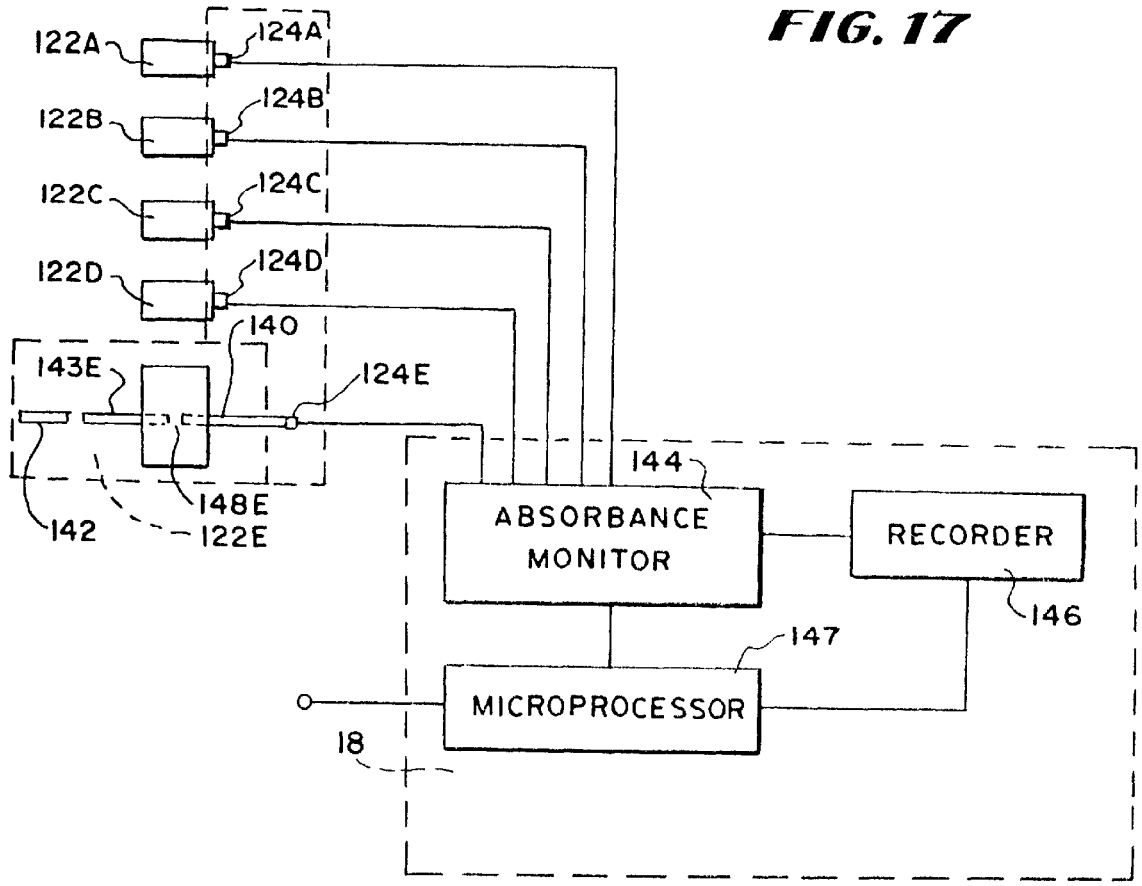
FIG. 17 is a block diagram illustrating the detection of fluid in accordance with an embodiment of the invention.

In FIG. 17, there is shown a block diagram of the flow cells 122A–122E, the detectors 124A–124E and the controller 18 interconnected to illustrate some aspects of the invention that are applicable to the flow cells 122R, 122A–122J and detectors 124R, 124A–124J. As best shown in FIG. 17, the flow cell 122E includes a first light guide 143E, a second light guide 140E and the flow path 148E for effluent through the flow cell 122E. As shown in this view, the two light guides 143E and 140E are positioned adjacent to each other and in close proximity with the flow path 148E extending around it with sufficient volume to permit bubbles to pass around the space between the light guides 143E and 140E rather than blocking the path in the light guides. The light guide 143E is in communication at one end with the light guide 140E with the fluid in the flow cell 122E and at its opposite end with a photodiode detector 124E to detect light absorbance within the flow path 148E. This signal is applied with appropriate buffering to the controller 18.

The controller 18 includes inter alia an absorbance monitor 144, a recorder 146 and a microprocessor 147. The absorbance monitor 144 receives light from the detectors 124A–124E indicating the light that is absorbed and applies it to the microprocessor 147 which converts it to a logarithmic current. The recorder 146 may be utilized to record the bands of effluent but because the application of this chromatographic system is principally preparatory the recorder 146 will be unnecessary for most applications. The microprocessor 147 may be an Intel 80C196KC available from Intel Corporation, 1501 S. Mopac Expressway, Suite 400, Austin, Tex. 78746.

Figure 18:
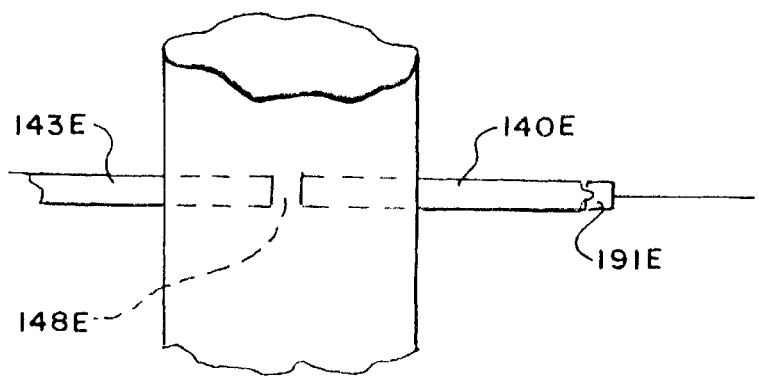

In FIG. 18 there is shown an enlarged, fragmentary perspective view of the flow cell 122E. The distance between the end of the light guide 143E and the end of the light guide 140E in the flow path 148E is approximately 0.1 mm (millimeters) in the preferred embodiment and should be in the range of 0.02 mm to 5 mm. It must be close enough to pass light between the two ends without excessive refraction or attenuation to prevent detection and far enough to provide a measure of absorbance sufficient to indicate the solute.

Figure 19:
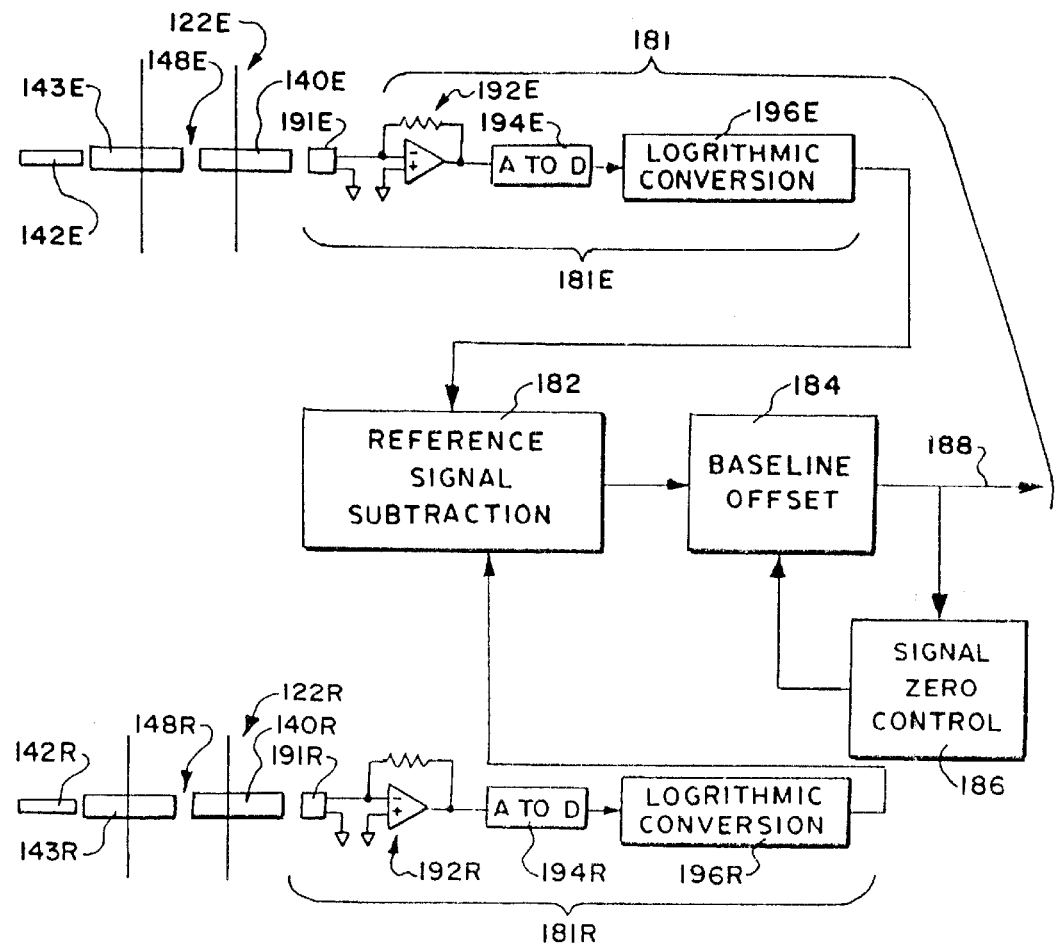
FIG. 19 is a schematic drawing showing a portion of the optical system in accordance with an embodiment of the invention.

In FIG. 19, there is shown a block diagram of a flow cell 122E and the reference flow cell 122R (dry cell with no fluid for reference purposes) connected to a calibration system to establish an absorbance signal, adjusted to provide a zero baseline. As best shown if FIG. 19, the flow cell 122E has within it a light guide 143E, which in the preferred embodiment is a quartz rod, on one side and on the other side another quartz rod 140E positioned with its end close to the end of the quartz rod 143E to provide a short space between them for the flow of fluid 148E in the flow path 148 and a large area around them for the flow of the liquid and any bubbles that may be in it. The quartz rod 143E abuts or nearly abuts the end of the light conductor 142E to receive light for transmission through the fluid 148E and into the light conductor 142E. Similarly, the flow cell 122R has the light conductor 142R abutting a quartz rod 143R which is inside the flow cell 122R and closely adjacent to the end of another quartz rod 140R for receiving light transmitted by the quartz rod 143R.

The light transmitted by the quartz rods 140E and 140R is converted to an electrical signal by the photodiode 191E and 191R respectively. This signal is conducted through the circuits 181E and 181R respectively transmitting it for absorbance in the fluid 148R to the circuit 181. The space between light conductors and the quartz light guide and between the photodiode and light guide is as short as possible to permit focusing in the case of different diameters. If the same diameter, they would touch but are separated slightly to permit the light from the small diameter to expand to the larger diameter or vice versa.

To receive and correct the signal from the flow cell such as 122E with respect to the reference 148R, the circuit 181 includes the signal receiving circuits 181E and 181R to receive and process the signal from the flow cells such as the flow cell 122E with respect to the reference signal from the reference flow cell 122R. The signal receiving circuit 181E includes a photodiode detector 191E, and amplifier 192E and analog-to-digital converter 194E and a logarithmic conversion circuit 196E.

The photodiode detector 191E abuts the quartz rod 140E to convert the absorbance signal from the fluid 148E to an electrical signal, which is amplified in the amplifier 192E and converted to a digital signal. The digital signal is converted to a logarithmic signal of the received signal in the converter 196E by a standard digital conversion in the microprocessor and transmitted to one side of a reference signal subtracter. Similarly, the signal receiving circuit 181R includes a photodiode detector 191R for receiving the reference signal from the reference flow cell 148R and converting it to an electric signal.

The electric signal is amplified by an amplifier 192R connected to the photodiode detector 191R and transmitted to the analog-to-digital converter 194R which in turn transmits a digital signal representing absorbance to the logarithmic of the received signal in the converter 196E by a standard digital conversion in the microprocessor and transmitted to one side of a reference signal subtracter. The reference signal subtracter subtracts the reference signal from the reference flow cell 122R from the absorbance signal from the flow cell 122E, resulting in a signal representing the absorbance which is transmitted to a reference off-set circuit 184. The reference off-set circuit 184 transmits a signal to a signal zero control circuit 186 that by subtracting a baseline constant in a manner known in the art and transmits the corrected absorbance signal through the conductor 188. In the preferred embodiment, there is a reference cell of the ten measuring flow cells and the necessary calculations are performed in a microprocessor.

The flow cells 122R and 122A–122J have a very short pathlength for the light, which allows very concentrated samples to be monitored. This short pathlength is accomplished by inserting 2 millimeter diameter UV quartz rod light guides 143R, 143A–143J and 140R, 140A–140J into each of the corresponding ones of the flow streams 148R, 148A–148J with a very small gap between each pair of two rods (typically 0.1 mm). This allows a very short effective pathlength for the light, while also allowing unrestricted flow to the fluid around the quartz rods. The light guides 143R and 140R and light source from an optical fiber 142R is coupled to a blank (dry) flow cell 122R, which passes light to a reference detector 191R. The reference detector signal is used for background optical noise and drift subtraction on the remaining detector channels. For purposes of best noise and drift reduction, the optical fiber used for the reference is not one of the four outermost fibers in the nested array.

The measuring and reference photodiode signals are amplified with linear amplifiers 192R, 192A–192J (192E and 192R being shown in FIG. 19). This signal is converted to a digital information with analog-to-digital converters 194R, 194A–194J (194E and 194R being shown in FIG. 19). These digital signals are converted to logarithms in the converters 196R, 196A–196J (196E and 196R being shown in FIG. 19). Now the reference signal can be subtracted to compensate for lamp energy variations in the reference signal subtracter 182. Next the baseline offset value is subtracted in the off-set circuit 184. This zeroes out almost all absorbance due to optical imbalance, including that of refractive index (thermal) gradients in the clean solvent flowing through the system. The baseline offset value is determined at the beginning of the separation. The signal at the start of the separation does not contain any solutes. The signal is stored and subtracted from the signal for the duration of the separation. This results in the correct absorbance signal. Both analog and digital methods of accomplishing these signal conditioning tasks are well known in the art.

Current state of the art in optical fiber technology results in fibers that have a varying susceptibility to transmission degradation (solarization) in the UV spectrum. It is also desirable to leave the UV lamp on to improve lamp thermal stability and hence detection stability. To satisfy these conflicting requirements, the diffraction grating is programmed to focus visible light on the fiber optics bundle at all times except when an actual separation is occurring. It is also possible to move the grating to the far UV (below 100 nm) where the energy output of the lamp is negligible. This reduces the amount of time the fibers are exposed to UV thereby reducing solarization, greatly increasing the life of the optical fibers while allowing the lamp to remain on between separations.

Figure 20:
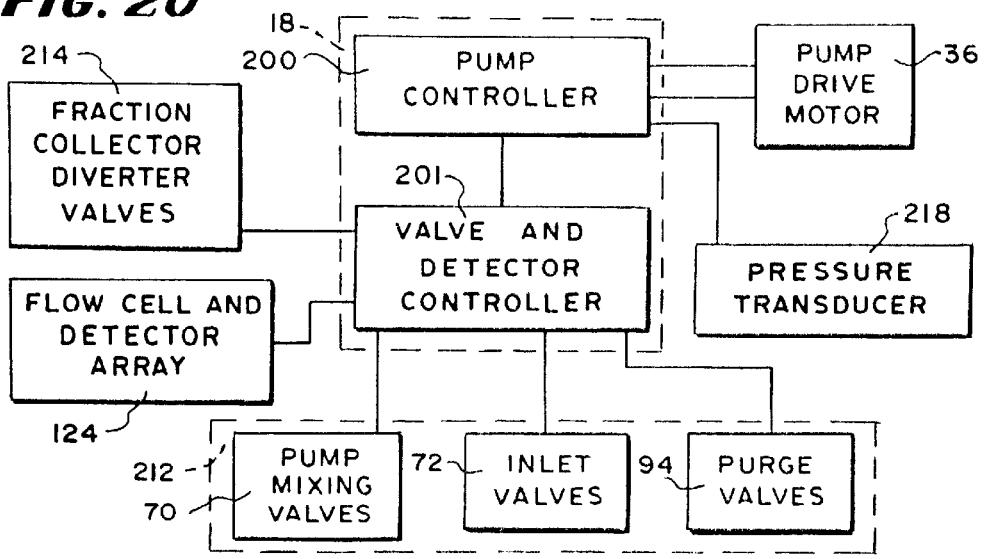
FIG. 20 is a block diagram showing the interconnections between portions of the preparatory chromatograph of an embodiment of the invention.

In FIG. 20, there is shown a block diagram having the fraction collector diverter valves 214, the flow cell and detector array 124, the controller 18, the pressure transducer 218 and the valve array 212 for the pumping system. This block diagram illustrates the connections between the controller 18, the pump drive motor 36, the fraction collector diverter valves 214, the flow cell and detector array 124, and the inlet purge and mixing valves 212. As shown in FIG. 20, the controller 18 includes inter alia functional components: the pump controller 200 and the valve and detector controller 201. The valve array 212 includes the pump mixing valves 70, the inlet valves 72 and the purge valve 94.

As shown in FIG. 20, the pump controller 200 is connected to the series pump drive 36 and a pressure transducer 218 in a feed-back arrangement such as that described in U.S. Pat. No. 5,360,320, the disclosure of which is incorporated herein by reference. Specifically, the feed-back circuit disclosed in connection with FIGS. 8 and 9 in columns 11, 12, 13 and 14 of U.S. Pat. No. 5,360,320 for controlling the pump disclosed in FIG. 4 of that patent is utilized here. The pump controller 200 also interacts with the valve and detector controller 201 to control the flow cell and detector array 124 and the fraction collector diverter valves 214 for the fraction collector 40 (FIG. 14). The valve and detector controller 201 supplies signals to control the mixing valves 70A–70J shown collectively at 70, the inlet valves 72A–72J shown collectively at 72 and the purge valve 94 of the valve array 212. With this arrangement, the detection of bands to be collected controls the fraction collector valves to channel the collection into appropriate containers.

Figure 21:
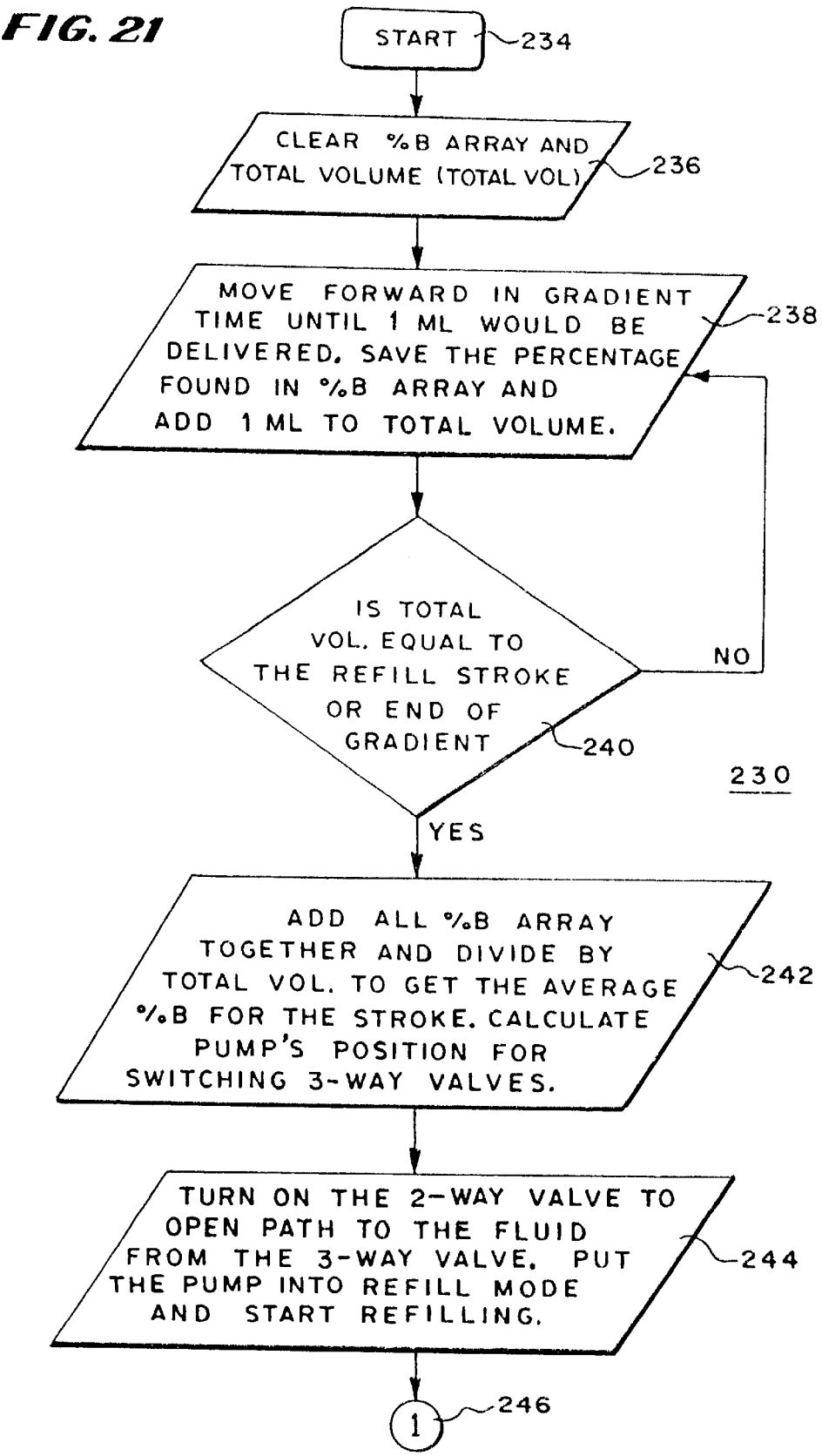
FIG. 21 is a flow diagram of a portion of a program utilized in an embodiment of the invention.
Figure 22:
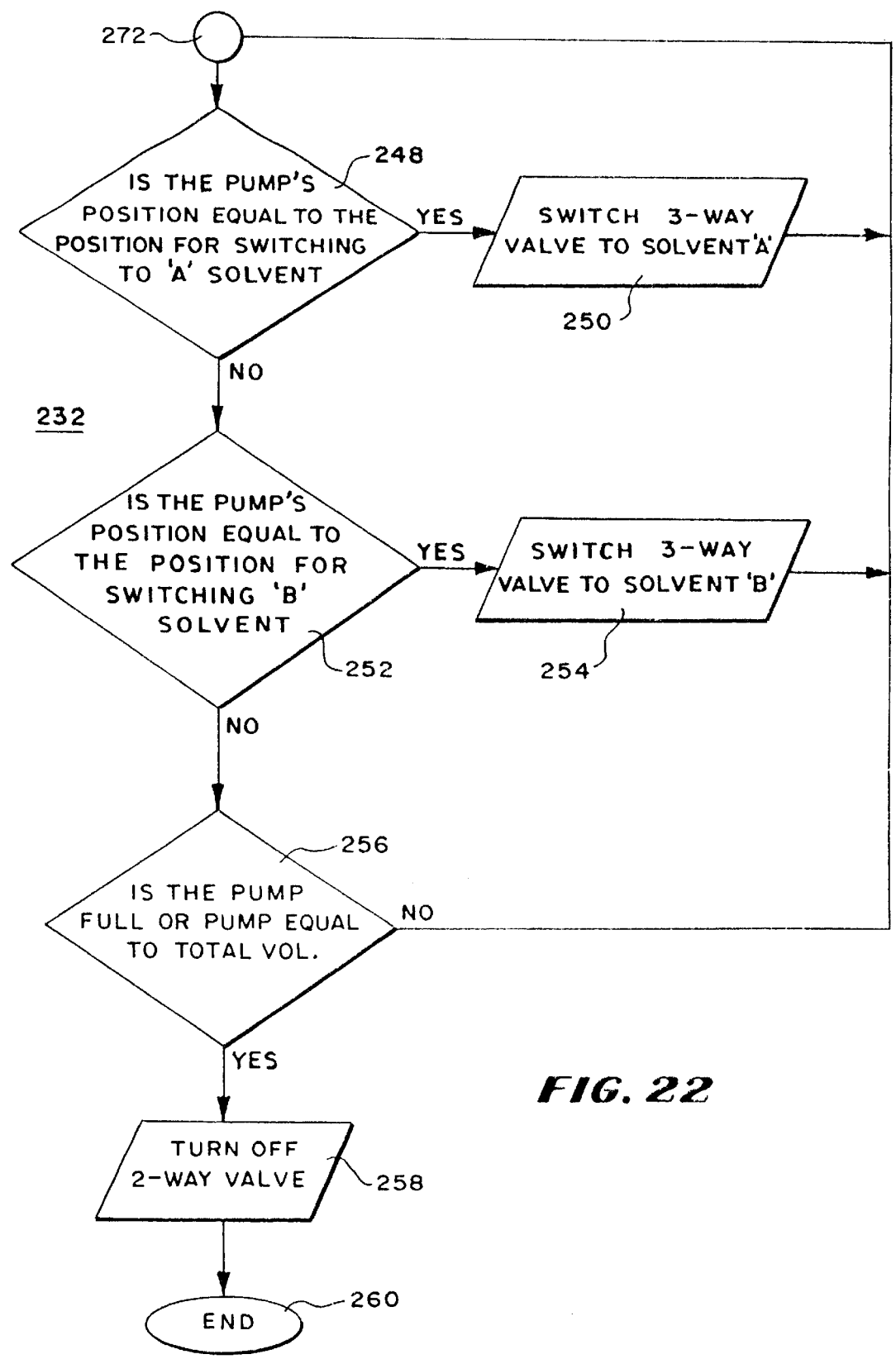
FIG. 22 is a flow diagram illustrating the performance of an embodiment of the invention.
Figure 23:
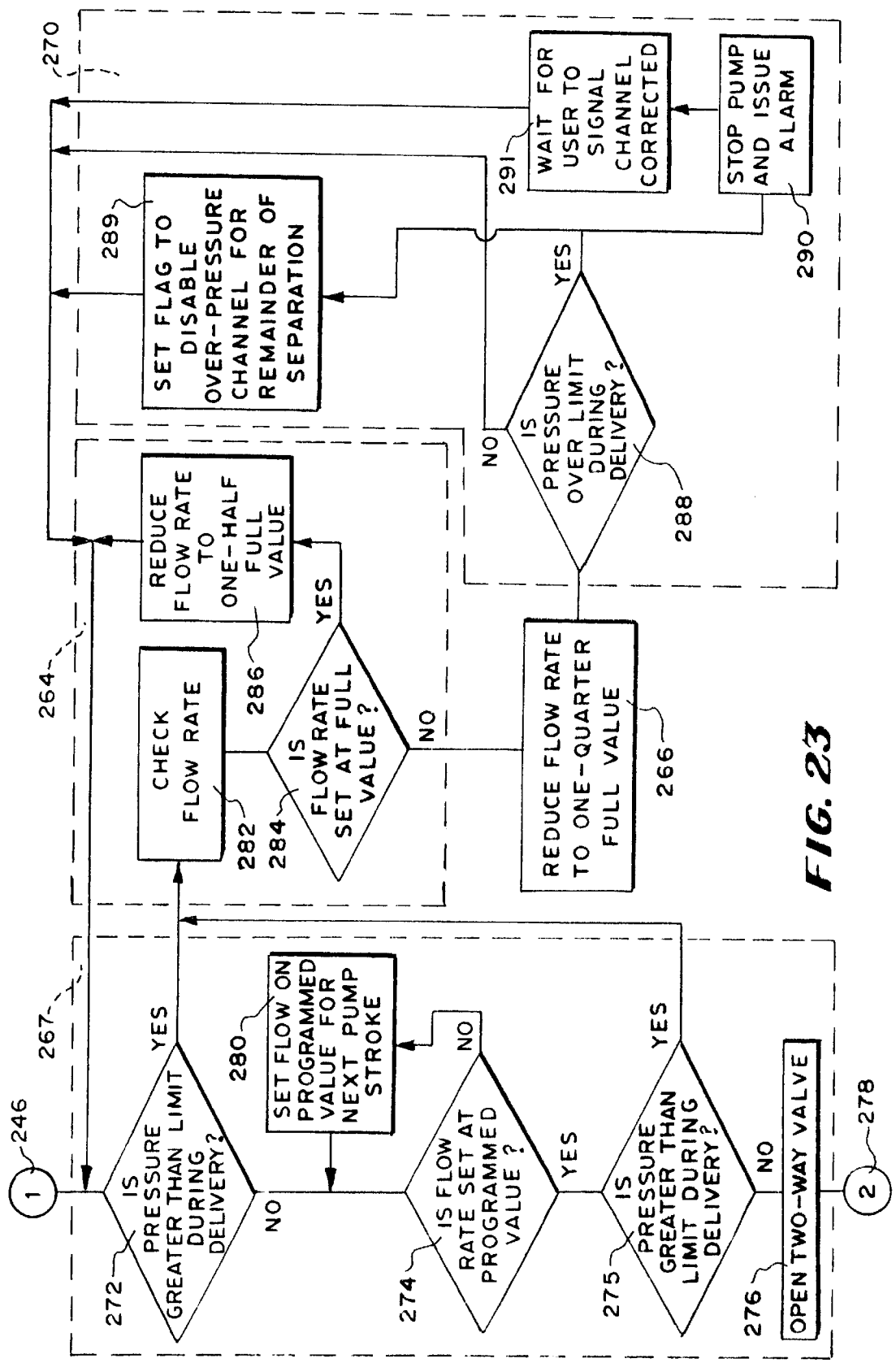
FIG. 23 is a flow diagram illustrating the operation of the pressure overload protection feature of the invention.

In FIGS. 21, 22 and 23, there are shown flow diagrams illustrating the operation of the controller 18 under software control having a series of programed steps 230 for initiating the pump fill cycle as shown in FIG. 21, a series of steps 232 for forming a gradient in the pump as shown in FIG. 22, and a series of steps 292 for protecting against over-pressure conditions. The series of steps 230 for initiating pump refill operation includes a start step 234, a clear-registers step 236 for percentage B solvent and total volume, a step 238 to move forward in gradient time until one milliliter is delivered except for the percentage found in percentage solvent B register and the percentage B solvent array and adding one milliliter to total volume, the step 240 of deciding if total volume is equal to the refill stroke or the end of the gradient, the step 242 of adding the percentage B solvent array together and dividing the two together to get the average percentage of B solvent to total solvent for the stroke and calculating the pumps position for switching three-way valves and the step 244 for turning on the two-way valve to open the path to the fluid from the three-way valve and putting the pump into the refill mode and start refilling. These steps proceed in succession as listed above.

As shown by the decision step 240, if the total volume is equal to the refill stroke or the end of the gradient, the step 240 goes to step 242 to add all percentage B solvent array values together and divide by total volume to get the average of B solvent to total solvent for the stroke and calculating the pumps position for switching the three-way valves. If the decision is no at decision step 240 then step 238 is repeated to move the pistons in the pump array forward in gradient time until one milliliter is delivered except for the percentage found in the percentage of B solvent to total solvent array and adding one milliliter to total volume.

When the pump is in the refill mode at the end of step 244 and refilling has started as shown at position 246 (FIG. 21), the program proceeds to step 248 (FIG. 22). Step 248 is a decision step deciding if the pumps position is equal to the position for switching to the A solvent. If it is then the program proceeds to step 250 to switch the three-way valve to solvent A and then returns to position 246. If the decision at step 248 is no, then the program proceeds to step 252 to decide if the pumps position is equal to the position for switching to the B solvent. If the decision is yes, then the program proceeds to step 254 to switch the three-way valve to solvent B and from there back to position 246. If the decision is no, then the step proceeds to decision step 256 to decide if the pump is full or the pump equal to the total volume. If the decision is no, then the program proceeds to step 246. If the decision at step 256 is yes, then the program proceeds to step 258 to turn off the two-way valve after which the program ends as shown at step 260.

In FIG. 23, there is shown a flow diagram of the program 292 for handling over-pressure conditions comprising: (1) a subroutine for normal non-over-pressure operation 262; (2) a subroutine 264 for over-pressure conditions that can be cured by reduced flow rate such as may occur when the preset flow rate is too high for the solvent and packing of the columns; (3) a subroutine 266 for handling more difficult over-pressure conditions; and (4) a subroutine 270 for stopping the pump in the case of a serious jam that must be physically corrected.

Under conditions in which the pressure is not beyond the preset pressure, the flow rate is controlled by a subroutine 262 that includes: (1) the starting position 246 (FIG. 21); (2) the decision step 272 for determining if the pressure is greater than the preset value; (3) the decision step 274 for determining if the flow rate is at its full value; (4) the step 280 of setting the flow rate if it is not at full value; (5) the step 275 of determining if the pressure is above its limit with the flow rate at full value; and (6) the step of opening the two-way valve 276 if the pressure is within limits and ending in the step 278 (FIG. 22). In the decision steps 272 and 275, if the pressure is greater than the preset value, the subroutine goes to the subroutine 264 for mild over-pressure conditions. If not, the subroutine proceeds to decision step 274 to determine if the flow rate is at full value. If it is not at full value then it proceeds to the step 280 to increase the flow rate and returns to the decision step 274. When the flow rate is at full value and the pressure is within limits, the subroutine proceeds to the step 276 of opening the two-way valve to begin gradient flow.

When there is over-pressure, the subroutine 264 includes the step of reading the flow rate 282 and the decision step 284 of determining if the flow rate is set at full value. If it is set at full value, it proceeds to the step 286 to reduce the flow rate to one-half of full value and then proceeds back to the subroutine 262 which determines again if the pressure is within limits.

If the flow rate or velocity is not set at full value because it has been reduced to one-halt then the program proceeds to the step 266 which reduces the flow rate to one-quarter the full value and then proceeds back to subroutine 262. If the pressure is still too high, it proceeds through subroutine 264 to subroutine 270 to either complete the run or stop the run and issue an alarm. The subroutine 270 includes the decision step 288 of determining if the pressure is greater than the preset value at one-quarter the flow rate, the step 290 of stopping the pumps and issuing an alarm so the operator may cure a serious blockage such as a jamming condition, the step 291 of waiting for the user to signal that the problem has been corrected and the step 289 of setting a flag to disable the over-pressure channel. In the decision step 288, if the pressure is greaterthan the preset value, the program proceeds to the step 290 to stop the pump and issue an alarm but if it is not greater then it proceeds to the subroutine 262. The subroutine 262 permits a pump cycle to be completed even if it is at a lower flow rate.

In operation, a plurality of simple syringe pumps are driven by the same motor to draw solvent simultaneously and pump the solvent simultaneously through a corresponding plurality of columns for separation and through a plurality of detectors for detecting solute and channeling it into a fraction collector for automatic collection. The solvent is pulled from one or more manifolds so that a plurality of flow streams may be pulled into the corresponding plurality of pumps from one or more solvent reservoirs to form a gradient. In the case of gradient elution, a valve opens to pull a first solvent into the cylinder and then switches to pull in a second solvent. In the preferred embodiment, when forming a gradient, the pump receives two cycles of flow from two reservoirs so that a valve will cause solvent to flow from a first reservoir into the pump cylinder and then, except at the starting point of the gradient, from a second cylinder to pull a first charge of solvent and repeats with the identical amount from the first cylinder and the second cylinder to form a second charge of solvent.

The solvents are pulled through a flow passageway 73A through 73H (only 73E being shown in FIGS. 3 and 7–12) that is less than one-tenth the volume of a charge. The flow is mostly in the transitional stage between laminar flow and bulk or turbulent flow in the passageway. The passageway has a diameter less than one-half of the diameter of a pump cylinder. The force and flow rate (velocity) is enough to cause turbulent mixing in the cylinder of the pump. In this manner, the gradient is mixed within the pump cylinder so that a first mixture is pumped from several pumps together into corresponding columns. If there is an interface between liquids, ft is degraded. It is pumped when the motor moves all of the pistons of the syringe pumps upwardly. This process is repeated but the gradient may gradually change so that in a series of steps, a gradient is supplied. The flow through the passageway 73E, which serves as a first mixer, produces good axial mixing and poor transverse mixing of flow on a small scale and the turbulent flow caused in the pump cylinder 74E, which serves as a second mixer, enhances transverse mixing and axial mixing on a larger scale. Larger scale in this specification means one charge into the cylinder has approximately one-tenth to one-half of the pump volume and small scale means one-eighth to one-hundredth pump volume—full displacement being taken as pump volume (18 ml in the preferred embodiment). Between these values the quality of the mixing is proportionately enhanced.

While simply designed syringe pumps are used in the preferred embodiment, any other kind of pump may be used. Moreover, only one cycle of flow of liquids into a pump may be used or several may be used. Similarly, it is not necessary for two cycles of the same mixture to be injected into a pump during each filling of the cylinder but more cycles or one cycle can be used as programmed. While in the preferred embodiment, a single motor drives all of the pistons, more than one array of pumps can be utilized with a motor driving a first plurality and a different motor driving a second plurality.

The columns are simple separation columns and one column is dedicated to each pump. After flowing through the column, the liquid flows into inexpensively constructed detectors in which light is applied through light guides into the flow cell and received by a light guide from the flow cell. Photodetector diodes are mounted directly against the ends of the receiving light guides to receive electrical signals just outside of the flow cell. The spacing of the light guides is such as to provide adequate detection for preparatory chromatograph and the flow cell is large enough so that while it detects absorbance of fluid flowing between the light guides, other fluid flows around the light guides so that if bubbles are formed in the flow cell, they will pass around the guides. The light guides are sufficiently close together so as to not receive large bubbles but to receive a substantial amount of light passed between the two light guides and be able to determine the amount of solute from the light that is absorbed.

A single lamp provides light which is applied to a condensing mirror from a central spot on the lamp and applied through an aperture plate to a focusing mirror which focuses on a diffraction grating positioned to select an appropriate frequency of light which is stable in a line applied to a slot. The plurality of light conductors to be applied to detectors are positioned along the narrow slot to receive stable light of substantially equal intensity for transmission to the detectors. The detected light is applied to a typical absorbance monitor which controls a fraction collector to collect the preparatory fractions. With this arrangement, since a large number of separations is being performed simultaneously, a substantial amount of solute can be obtained in a short time.

Although a preferred embodiment of the invention has been described with some particularity, it is to be understood that the invention may be practiced other than as specifically described. Accordingly, it is to be understood that, within the scope of the appended claims, the invention may be practiced other than as specifically described.

What is claimed is:

1. A liquid chromatographic system including:
   at least one pumping system;
   at least one detector;
   said pumping system supplying solvent to the at least one detector;
   said detector including a light source, at least one photodiode and at least one flow cell;
   a first light guide receiving light from said light source and transmitting it to said flow cell;
   a second light guide positioned to receive light from said first light guide and transmit it to the at least one photodiode;
   said first and second light guides each having one of its ends positioned within a flow cell with the one end of the first light guide being adjacent to the one end of the second light guide so that light passes from the one end of said first light guide through solute in said flow cell and into the one end of the second light guide, whereby light is diminished within said flow cell by absorbance by said solute; and
   an over-pressure system for compensating for pressures in a fluid above a preset pressure.

2. A liquid chromatographic system according to claim 1 wherein the over-pressure system reduces the rate of flow of a channel having the pressure above the preset pressure.

3. A liquid chromatographic system according to claim 1 wherein the over-pressure system includes a subsystem that tests for a flow rate at which the pressure is less than a predetermined pressure.

4. A liquid chromatographic system according to claim 3 in which said at least one pumping system includes at least two pumps and at least one pump motor whereby said at least two pumps are driven by said at least one pump motor and the over-pressure system includes a subsystem that shuts the at least one pump motor off when the subsystem that tests for a flow rate does not select a flow rate at which said pressure is below the preset pressure.

5. A liquid chromatographic system according to claim 1 in which the over-pressure system includes a subsystem that completes a pump cycle at a lower pumping rate by slowing the pumps upon detecting a pressure above a preset pressure and then restores the flow rate to its original rate.

6. A liquid chromatographic system according to claim 5 in which said ends of said first and second light guides are spaced in the region of 0.02 to 5 millimeters apart.

7. A liquid chromatographic system according to claim 5 in which said light source includes:
   at least one lamp;
   means for focusing light from said at least one lamp onto a diffraction grating;
   means for focusing light from the diffraction grating onto an opening; and
   at least some of a plurality of light guides having an end in said opening whereby said at least some of said plurality of light guides receive light from said diffraction grating.

8. A liquid chromatographic system in accordance with claim 5 including at least one column wherein:
   said at least one pumping system comprises a plurality of pumps;
   said at least one column comprising a plurality of columns, each of said plurality of columns communicating with a different one of said plurality of pumps;
   said at least one detector comprising a plurality of detectors, each of said plurality of detectors communicating with a different one of said plurality of columns, whereby each of said detectors detects a signal; and
   said plurality of detectors including a photodiode positioned against one end of said second light guide.

9. A liquid chromatographic system in accordance with claim 5 in which each of said first and second light guides is in intimate contact with a different photodiode.

10. A liquid chromatographic system in accordance with claim 1 further comprising:
    at least two sources of liquid;
    said at least one pumping system including at least two syringe pumps;
    at least one time-proportioning electronically controllable liquid gradient switching valve;
    said switching valve being connected to switch liquid flow from one or the other of said at least two sources of liquid to an inlet of at least one of said at least two syringe pumps;
    each of the said syringe pumps having a displacement of at least five milliliters; and
    said one of said syringe pumps having a discharge outlet connected to a sample injection device and thence to a chromatographic column.

11. A liquid chromatographic system according to claim 10 wherein the over-pressure system includes a subsystem that tests for a flow rate at which the pressure is less than a predetermined pressure.

12. A liquid chromatographic system according to claim 11 in which said at least two syringe pumps are driven by at least one pump motor and the over-pressure system includes a subsystem that shuts the at least one motor off when the subsystem that tests for a flow rate does not select a flow rate at which said pressure is below the preset pressure.

13. A liquid chromatographic system according to claim 10 in which the over-pressure system includes a subsystem that completes a pump cycle at a lower pumping rate until detecting a pressure above a preset pressure and then restores the flow rate to its original rate.

14. A liquid chromatographic system in accordance with claim 10 wherein each of said at least two syringe pumps includes a piston and a cylinder; said liquid chromatographic system including a moving carriage attached to at least two pistons, wherein movement of each of the pistons with respect to a corresponding cylinder is carried out by the moving carriage.

15. A liquid chromatographic system in accordance with claim 10 further including:
    a data system;
    a sample concentration detector having an electrical output;
    said data system including a recorder having an electrical recording output connection;
    a fraction collector having a plurality of containers and a timing cycle for depositing liquid in the containers; and
    the data system being electrically connected to the electrical output of said sample concentration detector and to the electrical recording output connection wherein a container charge timing cycle of the fraction collector is stopped during pump refill and restarted and run during liquid delivery of at least one of said at least two syringe pumps.

16. A liquid chromatographic system in accordance with claim 10 further including a first mixing means and a second mixing means wherein the first mixing means resides in a fluid flow path between the said at least one time-proportioning electronically controllable liquid gradient switching valve and the inlet of said at least one of said at least two syringe pumps and the second mixing means resides in a cylinder of the at least one of said at least two syringe pumps downstream of an inlet of the at least one time-proportioning electronically controllable liquid gradient switching valve.

17. A liquid chromatographic system in accordance with claim 16 wherein the fluid flow path between the at least one time-proportioning electronically controllable liquid gradient switching valve and the inlet of the at least one of said at least two syringe pumps is a flow passageway sized to produce mixing in the passageway, which in combination with mixing in the cylinder of the at least one of said two syringe pumps makes each step of gradient sufficiently flat and reproducible for a desired set of chromatographic separation processes.

18. A liquid chromatographic system in accordance with claim 17 wherein the flow passageway has a volume less than one-tenth that of a single charge, wherein the flow passageway has a diameter of less than one-half the diameter of the cylinder of the at least one of said at least two syringe pumps; said flow producing good axial mixing and poor transverse mixing on a small scale charge and an outlet of said flow passageway injecting into the cylinder of the at least one of said at least two syringe pumps where the flow becomes turbulent flow thus enhancing transverse mixing and axial mixing on a large scale.

19. A liquid chromatographic system in accordance with claim 18 wherein the flow passageway has a volume of at least one-tenth that of a single charge; said flow producing good axial mixing on a small scale and an outlet of said flow passageway injecting into the cylinder of the at least one of said at least two syringe pumps where the flow undergoes enhanced transverse mixing.

20. A liquid chromatographic system in accordance with claim 19 wherein the flow passageway has a volume of at least one-tenth that of a single charge, wherein the distance required for further transverse mixing is small; said flow producing good axial mixing and an outlet of said flow passageway injecting into a larger diameter pump cylinder where the flow becomes turbulent and undergoes transverse mixing and axial mixing.

21. A liquid chromatographic system in accordance with claim 10 in which said at least one time-proportioning electronically controllable liquid gradient switching valve is arranged to produce consecutive pulses of liquid from at least one of said at least two sources of liquid to a refill inlet at a fluid velocity high enough to induce turbulent mixing in a space between a head of a piston and that part of a cylinder not occluded by the piston.

22. A liquid chromatographic system according to claim 10 further comprising:
at least one motor;
said at least one pumping system including a plurality of pumps each having a corresponding one of a plurality of pistons and a corresponding one of a plurality of cylinders;
means connected to said at least one motor for driving at least some of said plurality of pistons, wherein said at least one motor includes one motor driving at least two pistons;
at least some of said plurality of cylinders being adapted to communicate with a source of solvent, whereby at least some of said plurality of pumps simultaneously pump a solvent driven by one motor;
at least one column;
at least some of said plurality of pumps communicating with at least one column, whereby solvent may be applied to said at least one column from at least some of said plurality of pumps;
at least one flow detector communicating with said at feast one column, whereby effluent from said at least one column may be detected; and
a controller communicating with said at least one detector, whereby effluent may be channeled to predetermined locations.

23. A liquid chromatographic system according to claim 22, wherein:
said at least one column is a plurality of columns;
different ones of said pumps communicating with corresponding ones of said columns, whereby solvent may be applied to said columns;
said at least one flaw detector is a plurality of flow detectors each communicating with a different one of said columns, whereby effluent from said columns may be detected; and
said controller communicating with said detectors, whereby effluent may be channeled to predetermined locations.

24. A liquid chromatographic system according to claim 1, further comprising:
a motor;
said at least one pumping system including a plurality of pumps;
a two way valve;
said pumps being adapted to be connected to the two-way valve;
said two-way valve being adapted to be connected alternately to a first solvent reservoir and a second solvent reservoir, whereby the amount of time said two-way valve is in a first position controls the amount of solvent drawn from said first solvent reservoir into said pumps and the amount of time in a second position controls the amount of solvent drawn from said second solvent reservoir into said pumps;
means for injecting said solvent into said pumps, whereby said solvent is further mixed in said pumps;
a plurality of columns;
a plurality of detectors;
each of said pumps communicating with a different column and a different detector; and
each of said detectors communicating with a controller, whereby said controller received signals indicating peaks.

25. The at least one pumping system in accordance with claim 1 further comprising:
at least one inlet tube;
said at least one pumping system including at feast one pump having a cylinder, a piston and a pump head with an outlet;
said at least one inlet tube having first and second ends communicating with the pump cylinder at one end and adapted to communicate with at least two sources of fluid at the other end;

said at least one inlet tube having a diameter and length shaped for flow; and drive means for driving said pump piston with sufficient speed to cause turbulent mixing in said pump cylinder, wherein fluid from said at least two sources of fluid are mixed before being pumped from an outlet.

26. A liquid chromatographic system in accordance with claim 1 further comprising:

at least one motor;

said pumping system including at least one pump connected to the at least one motor to be driven by the at least one motor;

at least one column connected to the at least one pump to receive fluid from the at least one pump;

a detector connected to detect solute in an effluent from said at least one column; and a collector positioned to receive the solute and deposit the solute into at least one container.

27. A liquid chromatographic system including:

at least one pumping system;

at least one detector;

said at least one pumping system supplying solvent to the at least one detector;

said at least one detector including at least one light source, at least one flow cell and at least one photodiode;

a first light guide receiving light from said light source and transmitting it to said flow cell;

a second light guide positioned to receive light from said first light guide and transmit it to the at least one photodiode;

said first and second light guides each having one of its ends positioned within a flow cell with the one end of the first light guide being adjacent to the one end of the second light guide so that light passes from the one end of said first light guide through solute in said flow cell and into the one end of the second light guide, whereby light is diminished within said flow cell by absorbance by said solute.

28. A liquid chromatographic system according to claim 27 in which said ends of said first and second light guides are spaced in the region of 0.02 to 5 millimeters apart.

29. A liquid chromatographic system according to claim 27 in which said light source includes:

at least one lamp;

means for focusing light from said at least one lamp onto a diffraction grating;

means for focusing light from the diffraction grating onto an opening; and at least some of a plurality of light guides having an end in said opening whereby said at least some of said plurality of light guides receive light from said diffraction grating.

30. A liquid chromatographic system in accordance with claim 27 including at least one column wherein:

said at least one pumping system comprises a plurality of pumps;

said at least one column comprising a plurality of columns, each of said plurality of columns communicating with a different one of said plurality of pumps;

said at least one detector comprising a plurality of detectors, each of said plurality of detectors communicating with a different one of said plurality of columns, whereby each of said detectors detects a signal; and said detectors each including a photodiode positioned against one end of said second light guide.

31. A liquid chromatographic system in accordance with claim 27 in which each of said light guides is in intimate contact with a different photodiode.

* * * * *